(12) United States Patent
Jayamani et al.

(10) Patent No.: US 11,122,828 B2
(45) Date of Patent: Sep. 21, 2021

(54) MICROBIAL COMPOSITIONS COMPRISING ELLAGITANNIN AND METHODS OF USE

(71) Applicant: MarvelBiome, Inc., Woburn, MA (US)

(72) Inventors: Elamparithi Jayamani, Malden, MA (US); Jothi Amaranath Govindan, Malden, MA (US); Priti H. Chatter, Concord, MA (US)

(73) Assignee: MarvelBiome, Inc., Woburn, MA (US)

(*) Notice: Subject to any disclaimer, the term of this patent is extended or adjusted under 35 U.S.C. 154(b) by 0 days.

(21) Appl. No.: 16/673,840

(22) Filed: Nov. 4, 2019

(65) Prior Publication Data

US 2020/0138075 A1 May 7, 2020

Related U.S. Application Data

(60) Provisional application No. 62/909,736, filed on Oct. 2, 2019, provisional application No. 62/755,880, filed on Nov. 5, 2018.

(51) Int. Cl.

| C12R 1/25 | (2006.01) |
|---|---|
| A23L 29/00 | (2016.01) |
| A23L 19/00 | (2016.01) |
| A23L 27/30 | (2016.01) |
| C12N 9/88 | (2006.01) |

(Continued)

(52) U.S. Cl.
CPC .............. *A23L 29/06* (2016.08); *A23L 19/00* (2016.08); *A23L 27/33* (2016.08); *A23L 29/065* (2016.08); *C12N 9/18* (2013.01); *C12N 9/88* (2013.01); *A23L 33/135* (2016.08);

*A23Y 2220/67* (2013.01); *C12R 1/25* (2013.01); *C12Y 301/0102* (2013.01); *C12Y 401/01059* (2013.01)

(58) Field of Classification Search
CPC ...... C12R 1/25; A23Y 2220/67; A23L 33/135
See application file for complete search history.

(56) References Cited

U.S. PATENT DOCUMENTS

| 5,225,202 A | 7/1993 | Hodges et al. |
| 5,733,575 A | 3/1998 | Mehra et al. |
| 6,139,875 A | 10/2000 | Adams et al. |

(Continued)

FOREIGN PATENT DOCUMENTS

| CN | 107418995 A | * 12/2017 |
| WO | WO-2015/186998 A1 | 12/2015 |

(Continued)

OTHER PUBLICATIONS

Adams, L. et al., Pomegranate Juice, Total Pomegranate Ellagitannins, and Punicalagin Suppress Inflammatory Cell Signaling in Colon Cancer Cells, J. Agric. Food Chem., 54:980-985 (2006).

(Continued)

*Primary Examiner* — Walter A Moore
(74) *Attorney, Agent, or Firm* — Choate, Hall & Stewart LLP; Sowmya Subramanian; Stephanie L. Schonewald

(57) ABSTRACT

A combination is provided comprising an ellagitannin composition, and an enzymatic composition comprising one or more ellagitannin enzymes, where the one or more ellagitannin enzymes comprise a tannin acyl hydrolase enzyme, a gallate decarboxylase enzyme, or a combination thereof. Methods of making and using combinations disclosed herein are also provided.

22 Claims, 5 Drawing Sheets

(51) Int. Cl.
C12N 9/18 (2006.01)
A23L 33/135 (2016.01)

(56) References Cited

U.S. PATENT DOCUMENTS

| | | | |
|---|---|---|---|
| 6,420,473 | B1 | 7/2002 | Chittamuru et al. |
| 6,455,052 | B1 | 9/2002 | Marcussen et al. |
| 6,569,457 | B2 | 5/2003 | Ullah et al. |
| 2009/0123979 | A1 | 5/2009 | Xu |
| 2016/0106789 | A1 | 4/2016 | Nofar et al. |

FOREIGN PATENT DOCUMENTS

| | | | | |
|---|---|---|---|---|
| WO | WO-2017/172766 | A1 | 10/2017 | |
| WO | WO-2018/217588 | A1 | 11/2018 | |
| WO | WO-2019/178542 | A1 | 9/2019 | |
| WO | WO-2019212997 | A1 * | 11/2019 | ........... A61K 31/366 |
| WO | WO-2020/096992 | A1 | 5/2020 | |

OTHER PUBLICATIONS

Aguilar, C. et al., A Comparison of Methods to Determine Tannin Acyl Hydrolase Activity, Braz. Arch. Biol. Technol., 42 (3), Curitiba (1999).
An, J.H. and Blackwell, T.K, SKN-1 links *C. elegans* mesendodermal specification to a conserved oxidative stress response, Genes & Development, 17(15):1882-1893 (2003).
Bajpai, B. and Patil, S., Tannin acyl hydrolase (EC 3.1.1.20) activity of Aspergillus, Penicillium, Fusarium and Trichoderma, World Journal of Microbiology & Biotechnology, 12:217-220 (1996).
Beverini, M. and Metche, M., Identification, Purification and Physicochemical Properties of Tannase of Aspergillus Orizae, Sci. Des. Aliments, 10:807-816 (1990).
Boer, E. et al., Atan Ip—an extracellular tannase from the dimorphic yeast *Arxula adeninivorans*: molecular cloning of the ATAN1 gene and characterization of the recombinant enzyme, Yeast, 26:323-337 (2009).
Cerda, B. et al., Thoe potent in vitro antioxidant ellagitannins from pomegranate juice are metabolised into bioavailable but poor antioxidant hydroxy-6H-dibenzopyran-6-one derivatives by the colonic microflora of healthy humans, Eur. J. Nutr., 43:205-220 (2004).
Curiel, J. et al., Production and Physicochemical Properties of Recombinant *Lactobacillus plantarum* Tannase, J. Agric. Food Chem., 57:6224-6230 (2009).
Fukui, Y. et al., Two novel blue pigments with ellagitannin moiety, rosacyanins A1 and A2, isolated from the petals of *Rosa hybrida*, Tetrahedron, 62:9661-9670 (2006).
Gonzalez-Barrio, R. et al., UV and MS Identification of Urolothins and Nasutins, the Bioavailable Metabolites of Ellagitannins and Ellagic Acid in Different Mammals, J. Agric. Food Chem. 59:1152-1162 (2011).
Gonzalez-Sarrias, A. et al., Gene expression, cell cycle arrest and MAPK signalling regulation in Caco-2 cells exposed to ellagic acid and its metabolites, urolithins, Mol. Nutr. Food Res., 53:686-698 (2009).
Haslam, E. et al. Gallotannins. Part I. Introduction: and the Fractionation of Tannase, J. Chem. Soc., 1829-1835 (1961).
Jimenez, N. et al., Uncovering the *Lactobacillus plantarum* WCFS1 Gallate Decarboxylase Involved in Tannin Degradation, Applied and Environmental Microbiology, 79(14):4253-4263 (2013).
Kell, A. et al., Activation of SKN-1 by novel kinases in Caenorhabditis elegans, Free Radic Biol Med., 43(11):1560-1566 (2007).
Landete, J. et al., Probiotic Bacteria for Healthier Aging: Immunomodulation and Metabolism of Phytoestrogens, Biomed Research International, 2017, 10 pages (2017).
Larrosa, M. et al, Urolithins, Ellagic Acid-Derived Metabolites Produced by Human Colonic Microflora, Exhibit Estrogenic and Antiestrogenic Activities, J. Agric. Fool Chem., 54:1611-1620 (2006).
Link, C. and Johnson, C., Reporter Transgenes for Study of Oxidant Stress in Caenorhabditis elegans, Meth Enzymol., 353:497-505 (2002).
Pacheco-Palencia, L. et al., Protective Effects of Standardized Pomegranate (*Punica granatum* L.) Polyphenolic Extract in Ultraviolet-Irradiated Human Skin Fibroblasts, J. Agric. Food Chem., 56:8434-8441 (2008).
Piwowarski, J. et al., Phase II Conjugates of Urolithins Isolated from Human Urine and Potential Role of β-Glucorinadaes in Their Disposition, Drug Metabolism and Disposition, 45(6):657-665 (2017).
Ren, B. et al., Crystal Structure of Tannase from *Lactobacillus plantarum*, J. Mol. Biol., 425:2737-2751 (2013).
Reveron, I. et al., Differential Gene Expression by *Lactobacillus plantarum* WCFS1 in Response to Phenolic Compounds Reveals New Genes Involved in Tannin Degradation, Applied and Environment Microbiology, 83(7):e03387-16 (2017).
Rodriguez, J. et al., Urolithin B, a newly regulator of skeletal muscle mass, Journal of Cachexia, Sarcopenia and Muscle, 8:583-597 (2017).
Rodriguez-Duran, L. et al., Novel Strategies for Upstream and Downstream Processing of Tannin Acyl Hydrolase, Enzyme Research, 823619, 20 pages (2011).
Seeram, N. et al., Rapid large scale purification of ellagitannins from pomegranate husk, a by-product of the commercial juice industry, Separation and Purification Technology, 41:49-55 (2004).
Selma, M. et. al., Description of urolithin production capacity from ellagic acid of two human intestinal *Gordonibacter* species, Food Func., 5:1779-1784 (2014).
Sharma, M. et al., Effects of Fruit Ellagitannin Extracts, Ellagic Acid, and Their Colonic Metabolite, Urolithin A, on Wnt Signaling, J. Agric. Food Chem., 58:3965-3969 (2010).
Skene, I.K. and Booker, J.D., Characterization of Tannin Acylhydrolase Activity in the Ruminal Bacterium Selenomonas Ruminantium, Anaerobe, 1:321-327 (1995).
Valero-Cases, E. et al., Influence of Fermentation with Different Lactic Acid Bacteria and in Vitro Digestion on the Biotransformation of Phenolic Compounds in Fermented Pomegranate Juices, J Agric Food Chem., 65(31):6488-6496 (2017).
Yamada, K. et al., Studies of Tannin Acyl Hydrolase of Microorganism, Agr. Biol. Chem. 45:233-240 (1967).
Zhang, Y. et al., Isolation and Identification of Strawberry Phenolics with Antioxidant and Human Cancer Cell Antiproliferative Properties, J. Agric. Food Chem., 56:670-675 (2008).
Zhang, Y. et al., Phyllanemblinins A-F, Ellagitannins from Pphyllanthus emblica, J. Nat. Prod., 64:1527-1532 (2001).
Zhong, X. et al., Secretion, purification, and characterization of a recombinant *Aspergillus oryzae* tannaase in *Pichia pastoris*, Protein Expression and Purification, 36:165-169 (2004).
International Search Report for PCT/US2019/059724 (Microbial Compositions Comprising Ellagitannin and Methods of Use, filed Nov. 4, 2019) received from ISA/US, 6 pages (dated Feb. 20, 2020).
Jimenez, N. et al., Tannin Degradation by a Novel Tannase Enzyme Present in Some *Lactoacillus plantarum* Strains, Applied and Environmental Microbiology, 80(10):2991-2997 (2014).
Papuc, C. et al., Plant Polyphenols as Antioxidant and Antibacterial Agents for Shelf-Life Extension of Meat and Meat Products: Classification, Structures, Sources, and Action Mechanisms, Comprehensive Reviews in Food Science and Food Safety, 16:1243-1268 (2017).
Written Opinion for PCT/US2019/059724 (Microbial Compositions Comprising Ellagitannin and Methods of Use, filed Nov. 4, 2019) received from ISA/US, 10 pages (dated Feb. 20, 2020).

* cited by examiner (A)

(B)

(A)

(B)

US 11,122,828 B2

MICROBIAL COMPOSITIONS COMPRISING ELLAGITANNIN AND METHODS OF USE

CROSS REFERENCE TO RELATED APPLICATIONS

This application claims priority to U.S. Provisional Patent Application No. 62/909,736, filed Oct. 2, 2019, and U.S. Provisional Patent Application No. 62/755,880, filed Nov. 5, 2018, the entire contents of both of which are hereby incorporated by reference in their entirety.

DEPOSIT OF BIOLOGICAL MATERIAL

The present specification makes reference to a biological deposit of wild-type strain *Lactobacillus plantarum* MBT501 (denoted strain "MBT501"), which was deposited at the American Type Culture Collection (ATCC®) in Manassas, Va. on Apr. 13, 2021 and designated Patent Deposit Number PTA-127009. The entire contents of the deposit are herein incorporated by reference.

BACKGROUND

Plant polyphenol compounds are a dietary source of antioxidants, implicated in a number of health benefits, including anti-inflammatory and anti-cancer activities.

SUMMARY

The present disclosure recognizes that metabolites of ellagitannins, including urolithins (e.g., urolithin A, urolithin B, urolithin C, urolithin D, and/or isourolithin A), can be beneficial to the health of, e.g., mammals, e.g., humans. However, it is generally understood in the art that metabolites of ellagitannins have low bioavailability. The present disclosure provides the insight that certain microbes, e.g., those expressing one or more ellagitannin enzymes can be provided in a combination with an ellagitannin composition. Among other things, the present disclosure provides that a combination of microbes expressing one or more ellagitannin enzymes and an ellagitannin composition can increase the bioavailability of metabolites of ellagitannins, including urolithins (e.g., urolithin A, urolithin B, urolithin C, urolithin D, and/or isourolithin A).

In some embodiments, a combination provided herein can comprise an ellagitannin composition, and an enzymatic composition. In some embodiments, an enzymatic composition can comprise one or more ellagitannin enzymes.

In some embodiments, one or more ellagitannin enzymes can comprise a tannin acyl hydrolase enzyme, a gallate decarboxylase enzyme, or a combination thereof. In some embodiments, one or more ellagitannin enzymes can comprise a tannin acyl hydrolase enzyme. In some embodiments, a tannin acyl hydrolase enzyme is or includes a tan B tannase enzyme. In some embodiments, one or more ellagitannin enzymes can comprises a gallate decarboxylase enzyme. In some embodiments, a gallate decarboxylase enzyme is or includes an lpdB gallate decarboxylase enzyme. In some embodiments, a gallate decarboxylase enzyme is or includes an lpdC gallate decarboxylase enzyme. In some embodiments, one or more ellagitannin enzymes comprise an lpdB gallate decarboxylase enzyme and an lpdC gallate decarboxylase enzyme. In some embodiments, one or more ellagitannin enzymes comprises a tan B tannase enzyme, an lpdB gallate decarboxylase enzyme, and an lpdC gallate decarboxylase enzyme.

In some embodiments, an enzymatic composition comprises an ellagitannin-enzyme-synthesizing (EES) microbe or an extract thereof. In some embodiments, an EES microbe is found in nature. In some embodiments, an EES microbe is an engineered EES microbe. In some embodiments, an engineered EES microbe comprises a genetic alteration relative to an otherwise comparable reference microbe so that the engineered EES microbe produces the one or more ellagitannin enzymes at an absolute or relative level different from that of the reference microbe.

In some embodiments, an EES microbe is a member of the Lactobacillaceae family. In some embodiments, a member of the Lactobacillaceae family is a *L. plantarum* species.

In some embodiments, an EES microbe is viable or alive. In some embodiments, an EES microbe is lyophilized.

In some embodiments, a combination includes a sufficient amount of an EES microbe to colonize the microbiome of a subject.

In some embodiments, an ellagitannin composition comprises a plant extract of pomegranate, strawberry, raspberry, cranberry, blackberry, cloudberry, artic blackberry, muscadine grapes, guava, a Myrtaceae family fruit, walnut, pecan, chestnut, cashew, almond, pistachio, hazelnut, brazil nut, macadamia red wine aging in oak barrels, muscadine grapes juice, pomegranate juice, tea, cognac, Indian gooseberry, beefsteak fungus, or combinations thereof. In some embodiments, a combination includes an amount of an ellagitannin composition sufficient to induce expression, activity, or both of one or more ellagitannin enzymes in the EES microbe.

In some embodiments, an ellagitannin composition and one or more ellagtitannin enzymes are present in an amount effective to promote urolithin production in a subject.

In some embodiments, a combination comprises a prebiotic. In some embodiments, a combination comprises a fructooligosaccharide, an inulin, an isomaltooligosaccharide, a lactilol, a lactosucrose, a lactulose, a soy oligosaccharide, a transgalactooligosaccharide, a xylooligosaccharide, or a combination thereof.

In some embodiments, an ellagitannin composition, an enzymatic composition, or both can be formulated for oral administration. In some embodiments, an ellagitannin composition, an enzymatic composition, or both can be a food, a beverage, a feed composition, or a nutritional supplement. In some embodiments, an ellagitannin composition, an enzymatic composition, or both can be a liquid, syrup, tablet, troche, gummy, capsule, powder, gel, or film.

In some embodiments, a combination is formulated for oral administration. In some embodiments, a combination is a food, a beverage, a feed composition, or a nutritional supplement. In some embodiments, a combination is a liquid, syrup, tablet, troche, gummy, capsule, powder, gel, or film.

In some embodiments, a combination comprises a pharmaceutically acceptable carrier. In some embodiments, a combination is an enteric-coated formulation.

The present disclosure provides methods comprising administering a combination disclosed herein to a subject.

The present disclosure provides methods comprising administering to a subject an ellagitannin composition, an enzymatic composition comprising one or more ellagitannin enzymes, or a combination as disclosed herein so that the subject is receiving a combination disclosed herein.

In some embodiments, a method is a method of decreasing the formation of polypeptide aggregates in a cell or tissue. In some embodiments, a method is a method of decreasing an amount of polypeptide aggregates in a cell or tissue. In some embodiments, polypeptide aggregates are aggregates of polypeptide comprising a polyQ region (i.e., polyQ aggregates). In some embodiments, a polyQ region comprises at least 10, at least 20, at least 30, at least 40, or at least 50 glutamines. In some embodiments, a cell is or comprises neurons. In some embodiments, a cell is or comprises central nervous system tissue.

In some embodiments, a method comprises determining a level of polypeptide aggregate formation in a cell or tissue. In some embodiments, a method comprises comparing a level of polypeptide aggregate formation in a cell or tissue to a reference level of polypeptide aggregate formation in a cell or tissue. In some embodiments, a reference level is determined in a cell or tissue of a subject that has not been administered an ellagitannin composition, an enzymatic composition comprising one or more ellagitannin enzymes, or a combination as disclosed herein. In some embodiments, a method comprises, prior to administration, determining a level of polypeptide aggregate formation in a cell or tissue. In some embodiments, a method comprises, following administration, determining a level of polypeptide aggregate formation in a cell or tissue. In some embodiments, a method comprises comparing a level of polypeptide aggregate formation in a cell or tissue determined prior to administration with a level of polypeptide aggregate formation in a cell or tissue determined following administration.

In some embodiments, a method comprises determining a level of polypeptide aggregates in a cell or tissue. In some embodiments, a method comprises comparing a level of polypeptide aggregates in a cell or tissue to a reference level of polypeptide aggregates in a cell or tissue. In some embodiments, a reference level is determined in a cell or tissue of a subject that has not been administered an ellagitannin composition, an enzymatic composition comprising one or more ellagitannin enzymes, or a combination as disclosed herein. In some embodiments, a method comprises, prior to administration, determining a level of polypeptide aggregates in a cell or tissue. In some embodiments, a method comprises, following administration, determining a level of polypeptide aggregates in a cell or tissue. In some embodiments, a method comprises comparing a level of polypeptide aggregates in a cell or tissue determined prior to administration with a level of polypeptide aggregates in a cell or tissue determined following administration.

In some embodiments, a method is a method of modifying a level of one or more urolithins produced in the gut of the subject.

In some embodiments, a method comprises determining a level of the one or more urolithins produced in the gut of the subject. In some embodiments, a method comprises comparing the level of each of one or more urolithins produced in the gut of the subject to a corresponding reference level.

In some embodiments, a method comprises determining a level of one or more urolithins produced in plasma of a subject. In some embodiments, a method comprises comparing the level of one or more urolithins in plasma of a subject to a reference level. In some embodiments, a reference level is a concentration of a urolithin in plasma, e.g., 0.2-20 µM (Espin J C, Larrosa M, Garcia-Conesa M T, Tomás-Barberán F. Biological significance of urolithins, the gut microbial ellagic Acid-derived metabolites: the evidence so far. Evid Based Complement Alternat Med. 2013; 2013: 270418. doi:10.1155/2013/270418, which is incorporated herein by reference). In some embodiments, a reference level is a concentration of urolithin in plasma of at least 0.1 µM, at least 0.2 µM, at least 0.5 µM, at least 1 µM, at least 5 µM, at least 10 µM, or at least 15 µM. In some embodiments, a reference level is a concentration of urolithin in plasma of at least 0.5 µM, at most 1 µM, at most 5 µM, at most 10 µM, at most 15 µM, at most 20 µM, or at most 25 µM.

In some embodiments, a reference level, whether in gut or plasma, is a historical reference level of a urolithin, a urolithin level of in the gut of the subject prior to receiving a combination, or a urolithin level of in the gut of a comparable subject who has not received a combination.

In some embodiments, a method is a method of increasing an amount of a urolithin produced in the gut of the subject. In some embodiments, a urolithin is urolithin A (3,8-dihydroxyurolithin), urolithin C (3,8,9 trihydroxyuolithin), Isourolithin A (3,9 dihydroxyuolithin) urolithin B (3-hydroxyuolithin), urolithin D (3,4,8,9-tetrahydroxyurolithin) or a combination thereof.

In some embodiments, a method comprises determining an indicator of mitochondrial function in the subject. In some embodiments, a method comprises determining a level of mitophagy in a subject.

In some embodiments, a method is a method of modifying an expression level or an activity level of Nrf2 in a cell or tissue of a subject. In some embodiments, a method is a method of increasing the expression level or the activity level of Nrf2 in the cell or tissue of the subject.

In some embodiments, a method comprises determining the expression level or the activity level of nuclear respiratory factor-2 (Nrf2) in the cell or tissue of the subject. In some embodiments, a method comprises comparing the expression level or the activity level of Nrf2 in the cell or tissue to a reference level. In some embodiments, a reference level is a historical expression or activity level of Nrf2, an expression level or an activity level of nuclear respiratory factor-2 (Nrf2) in a comparable cell or tissue of the subject prior to receiving the combination, or an expression level or an activity level of nuclear respiratory factor-2 (Nrf2) in a comparable cell or tissue of a comparable subject who has not received the combination. In some embodiments, a method comprises determining an expression level or an activity level of a gene regulated by Nrf2 expression in a cell or tissue of the subject.

In some embodiments, a method comprises determining a level of one or more antioxidants in a cell or tissue of the subject. In some embodiments, a cell or tissue of a subject comprises a liver cell or liver tissue. In some embodiments, a method comprises measuring an indicator of liver health or function in a subject.

In some embodiments, a method is a method of increasing the bioavailability of an ellagitannin composition for a subject. In some embodiments, a method comprises determining a bioavailability level of an ellagitannin of the ellagitannin composition in the gut of a subject. In some embodiments, a method comprises comparing the bioavailability level of the ellagitannin of the ellagitannin composition in the gut of the subject to a reference level. In some embodiments, a reference level is a historical bioavailability reference level for a ellagitannin, a bioavailability level of an ellagitannin in the gut of the subject prior to receiving a combination; or a bioavailability level of an ellagitannin in the gut of a comparable subject who has not received the combination.

In some embodiments, a method is a method of treating a condition or disorder associated with mitochondrial dysfunction in a subject.

In some embodiments, a method is a method of treating a liver condition, disease, or disorder in a subject.

In some embodiments, a method is a method of increasing the viable shelf-life of a probiotic product comprising an EES microbe, comprising adding an ellagitannin composition to the probiotic product, where the EES microbe expresses one or more ellagitannin enzymes.

In some embodiments, one or more ellagitannin enzymes can comprise a tannin acyl hydrolase enzyme, a gallate decarboxylase enzyme, or a combination thereof. In some embodiments, one or more ellagitannin enzymes can comprise a tannin acyl hydrolase enzyme. In some embodiments, a tannin acyl hydrolase enzyme is or includes a tan B tannase enzyme. In some embodiments, one or more ellagitannin enzymes can comprises a gallate decarboxylase enzyme. In some embodiments, a gallate decarboxylase enzyme is or includes an lpdB gallate decarboxylase enzyme. In some embodiments, a gallate decarboxylase enzyme is or includes an lpdC gallate decarboxylase enzyme. In some embodiments, one or more ellagitannin enzymes comprise an lpdB gallate decarboxylase enzyme and an lpdC gallate decarboxylase enzyme. In some embodiments, one or more ellagitannin enzymes comprises a tan B tannase enzyme, an lpdB gallate decarboxylase enzyme, and an lpdC gallate decarboxylase enzyme.

In some embodiments, an enzymatic composition comprises an ellagitannin-enzyme-synthesizing (EES) microbe or an extract thereof. In some embodiments, an EES microbe is found in nature. In some embodiments, an EES microbe is an engineered EES microbe. In some embodiments, an engineered EES microbe comprises a genetic alteration relative to an otherwise comparable reference microbe so that the engineered EES microbe produces the one or more ellagitannin enzymes at an absolute or relative level different from that of the reference microbe.

In some embodiments, an EES microbe is a member of the Lactobacillaceae family. In some embodiments, a member of the Lactobacillaceae family is a *L. plantarum* species.

In some embodiments, an EES microbe is viable or alive. In some embodiments, an EES microbe is lyophilized.

In some embodiments, an engineered EES microbe comprises a genetic alteration relative to an otherwise comparable reference microbe so that it produces the one or more ellagitannin enzymes at an absolute or relative level different from that of the reference microbe.

In some embodiments, an ellagitannin composition comprises a plant extract of pomegranate, strawberry, raspberry, cranberry, blackberry, cloudberry, artic blackberry, muscadine grapes, guava, a Myrtaceae family fruit, walnut, pecan, chestnut, cashew, almond, pistachio, hazelnut, brazil nut, macadamia red wine aging in oak barrels, muscadine grapes juice, pomegranate juice, tea, cognac, Indian gooseberry, beefsteak fungus, or combinations thereof. In some embodiments, an ellagitannin composition comprises a supplement containing one or more ellagitannins or ellagic acids. In some embodiments, a combination includes an amount of an ellagitannin composition sufficient to induce expression, activity, or both of one or more ellagitannin enzymes in the EES microbe.

In some embodiments, an ellagitannin composition and one or more ellagitannin enzymes are present in an amount effective to promote urolithin production in a subject.

In some embodiments, a method comprises adding a prebiotic. In some embodiments, a prebiotic comprises a fructooligosaccharide, an inulin, an isomaltooligosaccharide, a lactilol, a lactosucrose, a lactulose, a soy oligosaccharide, a transgalactooligosaccharide, a xylooligosaccharide, or a combination thereof.

In some embodiments, a probiotic composition can be formulated for oral administration. In some embodiments, a probiotic composition can be a food, a beverage, a feed composition, or a nutritional supplement. In some embodiments, an ellagitannin composition, an enzymatic composition, or both can be a liquid, syrup, tablet, troche, gummy, capsule, powder, gel, or film. In some embodiments, a probiotic composition is an enteric-coated formulation.

The present disclosure provides a probiotic product comprising an EES microbe that expresses one or more ellagitannin enzymes. In some embodiments, one or more ellagitannin enzymes can comprise a tannin acyl hydrolase enzyme. In some embodiments, a tannin acyl hydrolase enzyme is or includes a tan B tannase enzyme. In some embodiments, one or more ellagitannin enzymes can comprises a gallate decarboxylase enzyme. In some embodiments, a gallate decarboxylase enzyme is or includes an lpdB gallate decarboxylase enzyme. In some embodiments, a gallate decarboxylase enzyme is or includes an lpdC gallate decarboxylase enzyme. In some embodiments, one or more ellagitannin enzymes comprise an lpdB gallate decarboxylase enzyme and an lpdC gallate decarboxylase enzyme. In some embodiments, one or more ellagitannin enzymes comprises a tan B tannase enzyme, an lpdB gallate decarboxylase enzyme, and an lpdC gallate decarboxylase enzyme.

In some embodiments, an EES microbe is found in nature. In some embodiments, an EES microbe is an engineered EES microbe. In some embodiments, an engineered EES microbe comprises a genetic alteration relative to an otherwise comparable reference microbe so that the engineered EES microbe produces the one or more ellagitannin enzymes at an absolute or relative level different from that of the reference microbe.

In some embodiments, an EES microbe is a member of the Lactobacillaceae family. In some embodiments, a member of the Lactobacillaceae family is a *L. plantarum* species.

In some embodiments, an EES microbe is viable or alive. In some embodiments, an EES microbe is lyophilized.

In some embodiments, an engineered EES microbe comprises a genetic alteration relative to an otherwise comparable reference microbe so that it produces the one or more ellagitannin enzymes at an absolute or relative level different from that of the reference microbe.

In some embodiments, a probiotic comprises a prebiotic. In some embodiments, a prebiotic comprises a fructooligosaccharide, an inulin, an isomaltooligosaccharide, a lactilol, a lactosucrose, a lactulose, a soy oligosaccharide, a transgalactooligosaccharide, a xylooligosaccharide, or a combination thereof.

In some embodiments, a probiotic product is formulated for oral administration. In some embodiments, a probiotic product is a food, a beverage, a feed composition, or a nutritional supplement. In some embodiments, a probiotic product is a liquid, syrup, tablet, troche, gummy, capsule, powder, gel, or film.

In some embodiments, a probiotic product is an enteric-coated formulation.

The present disclosure provides a method of manufacturing a probiotic product comprising an EES microbe, comprising adding an ellagitannin composition to the probiotic product, where the EES microbe expresses one or more ellagitannin enzymes.

In some embodiments, a method comprises adding a prebiotic. In some embodiments, a prebiotic comprises a fructooligosaccharide, an inulin, an isomaltooligosaccharide, a lactilol, a lactosucrose, a lactulose, a soy oligosaccharide, a transgalactooligosaccharide, a xylooligosaccharide, or a combination thereof.

The present disclosure provides uses of a combination disclosed herein for modulating a level of urolithin produced in the gut of a subject.

The present disclosure provides uses of a combination disclosed herein for regulating mitochondrial function in a subject.

The present disclosure provides uses of a combination disclosed herein for modulating a level of mitophagy in a subject.

The present disclosure provides uses of a combination disclosed herein for modulating an expression level or an activity level of Nrf2 in a cell or tissue of a subject.

The present disclosure provides uses of a combination disclosed herein for modulating an expression level or an activity level of a gene regulated by Nrf2 expression in a cell or tissue of a subject.

The present disclosure provides uses of a combination disclosed herein for modulating a level of one or more antioxidants in a cell or tissue of a subject. In some embodiments, a cell or tissue of a subject comprises a liver cell or liver tissue. The present disclosure provides uses of a combination disclosed herein for improving liver health or function in a subject.

The present disclosure provides uses of a combination disclosed herein for increasing a bioavailability level of an ellagitannin in the gut of a subject.

These, and other aspects encompassed by the present disclosure, are described in more detail below and in the claims.

Definitions

The scope of the present invention is defined by the claims appended hereto and is not limited by certain embodiments described herein. Those skilled in the art, reading the present specification, will be aware of various modifications that may be equivalent to such described embodiments, or otherwise within the scope of the claims. In general, terms used herein are in accordance with their understood meaning in the art, unless clearly indicated otherwise. Explicit definitions of certain terms are provided below; meanings of these and other terms in particular instances throughout this specification will be clear to those skilled in the art from context.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an," as used herein, should be understood to include the plural referents unless clearly indicated to the contrary. Claims or descriptions that include "or" between one or more members of a group are considered satisfied if one, more than one, or all of the group members are present in, employed in, or otherwise relevant to a given product or process unless indicated to the contrary or otherwise evident from the context. In some embodiments, exactly one member of a group is present in, employed in, or otherwise relevant to a given product or process. In some embodiments, more than one, or all group members are present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists (e.g., in Markush group or similar format), it is to be understood that each subgroup of the elements is also disclosed, and any element(s) can be removed from the group. It should be understood that, in general, where embodiments or aspects are referred to as "comprising" particular elements, features, etc., certain embodiments or aspects "consist," or "consist essentially of," such elements, features, etc. For purposes of simplicity, those embodiments have not in every case been specifically set forth in so many words herein. It should also be understood that any embodiment or aspect can be explicitly excluded from the claims, regardless of whether the specific exclusion is recited in the specification.

Administration: As used herein, the term "administration" typically refers to the administration of a composition to a subject or system to achieve delivery of an agent to the subject or system. In some embodiments, the agent is, or is included in, the composition; in some embodiments, the agent is generated through metabolism of the composition or one or more components thereof. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In many embodiments provided by the present disclosure, administration is oral administration. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time. Administration of cells can be by any appropriate route that results in delivery to a desired location in a subject where at least a portion of the delivered cells or components of the cells remain viable. A period of viability of cells after administration to a subject can be as short as a few hours, e.g., twenty-four hours, to a few days, to as long as several years, i.e., long-term engraftment. In some embodiments, administration comprises delivery of a bacterial extract or preparation comprising one or more bacterial metabolites and/or byproducts but lacking fully viable bacterial cells.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Approximately: As applied to one or more values of interest, includes to a value that is similar to a stated reference value. In certain embodiments, the term "approximately" or "about" refers to a range of values that fall within ±10% (greater than or less than) of the stated reference value unless otherwise stated or otherwise evident from the context (except where such number would exceed 100% of a possible value).

Bioavailability of ellagitannins: As used herein, the term "bioavailability of ellagitannins" refers to an amount of ellagitannins or products of their hydrolysis that are absorbed into systemic circulation from an ellagitannin composition. An amount of ellagitannins can be determined by measuring an amount of ellagitannin hydrolysis products present in blood, plasma, or urine samples. In addition, bioavailable ellagitannins may be metabolized in a subject to, e.g., urolithin. As such, bioavailability of ellagitannins can be determined indirectly by assessing an amount of urolithins in systemic circulation (e.g., blood, plasma, etc.) or excreted by the kidneys (e.g., urine). Thus, a change in (e.g., increase) bioavailability of a given ellagitannin composition can be determined by assessing levels of urolithin in the presence of an ellagitannin composition or combination as described herein. In some embodiments, levels of urolithin can be compared, e.g., to those of a subject prior to the onset of treatment with the composition.

Comparable: As used herein, the term "comparable" refers to two or more agents, entities, situations, sets of conditions, subjects, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Conservative: As used herein, refers to instances when describing a conservative amino acid substitution, including a substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine (Gly, G), alanine (Ala, A), valine (Val, V), leucine (Leu, L), and isoleucine (Ile, I); aliphatic-hydroxyl side chains such as serine (Ser, S) and threonine (Thr, T); amide-containing side chains such as asparagine (Asn, N) and glutamine (Gln, Q); aromatic side chains such as phenylalanine (Phe, F), tyrosine (Tyr, Y), and tryptophan (Trp, W); basic side chains such as lysine (Lys, K), arginine (Arg, R), and histidine (His, H); acidic side chains such as aspartic acid (Asp, D) and glutamic acid (Glu, E); and sulfur-containing side chains such as cysteine (Cys, C) and methionine (Met, M). Conservative amino acids substitution groups include, for example, valine/leucine/isoleucine (Val/Leu/Ile, V/L/I), phenylalanine/tyrosine (Phe/Tyr, F/Y), lysine/arginine (Lys/Arg, K/R), alanine/valine (Ala/Val, A/V), glutamate/aspartate (Glu/Asp, E/D), and asparagine/glutamine (Asn/Gln, N/Q). In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445, which is incorporated herein by reference in its entirety. In some embodiments, a substitution is a moderately conservative substitution wherein the substitution has a nonnegative value in the PAM250 log-likelihood matrix.

| CONSERVATIVE AMINO ACID SUBSTITUTIONS | | |
| --- | --- | --- |
| For Amino Acid | Code | Replace With |
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Control: As used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. A "control" also includes a "control animal." A "control animal" may have a modification as described herein, a modification that is different as described herein, or no modification (i.e., a wild-type animal). In one experiment, a "test" (i.e., a variable being tested) is applied. In a second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Determining, measuring, evaluating, assessing, assaying and analyzing: Determining, measuring, evaluating, assessing, assaying and analyzing are used interchangeably herein to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

Dosage form: Those skilled in the art will appreciate that the term "dosage form" may be used to refer to a physically discrete unit of an agent (e.g., a therapeutic agent) for administration to a subject. Typically, each such unit contains a predetermined quantity of agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population.

Ellagitannin-enriched: As used herein, the term "ellagitannin-enriched" refers to a material obtained by processing one or more plant materials, in which the fraction of one or more ellagitannins is increased relative to the fraction of the one or more ellagitannins in the plant material(s) before processing. Enrichment can be, for example, by at least 2-fold, at least 5-fold, at least 10-fold, at least 20-fold, or more.

Ellagitannin composition: As used herein, "ellagitannin composition" refers to a composition comprising one or more ellagitannin compounds. In some embodiments, an ellagitannin composition refers to an ellagitannin enriched substance. In some embodiments, an ellagitannin composition comprises pome extract. In some embodiments, an ellagitannin composition is produced by processing of one or more plant materials comprising one or more ellagitannin compounds made by one or more plants. In some embodiments, an ellagitannin composition includes juice of a fruit that produces an ellagitannin compound, a homogenate of a fruit or other material (e.g., skin, peel, husk, etc.) of a plant that produces an ellagitannin compound, an extract of a material from a plant that produces an ellagitannin compound, or an ellagitannin-enriched fraction of a juice, homogenate or extract of a plant that produces an ellagitannin compound. In some embodiments, an ellagitannin composition comprises a supplement containing one or more ellagitannins or ellagic acids.

Ellagitannin compound: As used herein, "ellagitannin compound" refers to compounds that are members of a diverse class of polyphenols, and structural analogs thereof. In nature, ellagitannins are hydrolyzed to ellagic acid, which is metabolized to produce different types of urolithins. Ellagitannins comprise a diverse class of complex hydrolyzable plant tannin polyphenols composed of hexahydroxydiphenoyl moieties esterified to a sugar, i.e., hexahydroxydiphenoyl-glucose esters, which can be found in a variety of foods such as strawberries (*Fragaria vesca*), raspberries, blackberries, cloudberries (*Rubus chamaemorus*), fruits of the Myrtaceae family, including, but not limited to j abuticaba, cambuci, Surinam cherries, camu-camu, red guava, white guava, pomegranate, walnuts, pecans, beefsteak fungus (*Fistulina hepatica*) and cranberries. Other ellagitannins include, for example, pedunculagins, rosacyanins, phyllanemblinins, and sanguiin H6.

Ellagitannin enzyme: As used here, "ellagitannin enzyme" refers to an enzyme involved in the metabolism of an ellagitannin to a urolithin. Ellagitannin enzymes include, but are not limited to: a tannin acyl hydrolase enzyme (e.g., a tan B tannase enzyme), and a gallate decarboxylase enzyme (e.g., an lpdB gallate decarboxylase enzyme, an lpdC gallate decarboxylase enzyme).

Ellagitannin-Enzyme-Synthesizing Microbe: As used herein, the phrase "ellagitannin-enzyme-synthesizing microbe" or "EES microbe" refers to a microbe (e.g., algae, fungi, bacteria) that expresses one or more ellagitannin enzymes. In some embodiments, an EES microbe may naturally express one or more ellagitannin enzymes. In some embodiments, an EES microbe includes an ellagitannin-enzyme modification. In some embodiments, an EES microbe may be genetically modified (e.g., to have one or more genetic alterations) so that it expresses one or more ellagitannin enzymes at an absolute or relative level different from that of an otherwise comparable reference microbe that has not been so genetically modified (i.e., does not contain the genetic alteration(s)). For example, in some embodiments, an EES microbe has been genetically engineered to express one or more ellagitannin enzymes not expressed by the microbe absent the genetic engineering. Alternatively, in some embodiments, an EES microbe may have been genetically engineered so that its expression of one or more ellagitannin enzymes may be at a higher level relative to the microbe absent the genetic engineering. In some embodiments, a higher level may be assessed in reference to a threshold level; in some embodiments, a higher level may be assessed in reference to another compound (e.g., another ellagitannin enzyme) also produced by the microbe (prior to the genetic engineering). In some particular embodiments, an EES microbe may have been genetically modified to add or increase expression of one or more genes encoding one or more ellagitannin enzymes.

Ellagitannin-enzyme modification: The term "ellagitannin-enzyme modification," as used herein, refers to a modification of a microbe that adjusts production of one or more ellagitannin enzymes, as described herein. For example, an ellagitannin-enzyme modification may increase the production level of one or more ellagitannin enzymes, and/or may alter relative production levels of different ellagitannin enzymes. In principle, an ellagitannin-enzyme modification may be any chemical, physiological, genetic, or other modification that appropriately alters production of one or more ellagitannin enzymes produced by a microbe as compared with the level produced in an otherwise identical microbe not subject to the same modification. In most embodiments, however, an ellagitannin-enzyme modification will comprise a genetic modification, typically resulting in increased production of one or more selected ellagitannin enzymes. In some embodiments, ellagitannin enzymes comprise a tannin acyl hydrolase enzyme (e.g., a tan B tannase enzyme), a gallate decarboxylase enzyme (e.g., an lpdB gallate decarboxylase enzyme, an lpdC gallate decarboxylase enzyme), or a combination thereof.

Engineered: In general, the term "engineered" refers to the aspect of having been manipulated by the hand of man. For example, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Excipient: As used herein, refers to an inactive (e.g., non-therapeutic) agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Functional: As used herein, a "functional" biological molecule is a biological molecule in a form in which it exhibits a property and/or activity by which it is characterized. A biological molecule may have two functions (i.e., bifunctional) or many functions (i.e., multifunctional).

Gene: As used herein, refers to a DNA sequence in a chromosome that codes for a product (e.g., an RNA product and/or a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). For the purpose of clarity, we note that, as used in the present disclosure, the term "gene" generally refers to a portion of a nucleic acid that encodes a polypeptide or fragment thereof; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid.

Improve, increase, enhance, inhibit or reduce: As used herein, the terms "improve," "increase," "enhance," "inhibit," "reduce," or grammatical equivalents thereof, indicate values that are relative to a baseline or other reference measurement. In some embodiments, a value is statistically significantly difference that a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment. In some embodiments, an appropriate reference is a negative reference; in some embodiments, an appropriate reference is a positive reference.

Isolated: As used herein, refers to a substance and/or entity that has been (1) separated from at least some of the components with which it was associated when initially produced (whether in nature and/or in an experimental setting), and/or (2) designed, produced, prepared, and/or manufactured by the hand of man. In some embodiments, an isolated substance or entity may be enriched; in some embodiments, an isolated substance or entity may be pure. In some embodiments, isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "enriched", "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. Those skilled in the art are aware of a variety of technologies for isolating (e.g., enriching or purifying) substances or agents (e.g., using one or more of fractionation, extraction, precipitation, or other separation).

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue, capsules, powders, etc. In some embodiments, an active agent may be or comprise a cell or population of cells (e.g., a culture, for example of an EES microbe); in some embodiments, an active agent may be or comprise an extract or component of a cell or population (e.g., culture) of cells. In some embodiments, an active agent may be or comprise an isolated, purified, or pure compound. In some embodiments, an active agent may have been synthesized in vitro (e.g., via chemical and/or enzymatic synthesis). In some embodiments, an active agent may be or comprise a natural product (whether isolated from its natural source or synthesized in vitro).

Pharmaceutically acceptable: As used herein, the term "pharmaceutically acceptable" which, for example, may be used in reference to a carrier, diluent, or excipient used to formulate a pharmaceutical composition as disclosed herein, means that the carrier, diluent, or excipient is compatible with the other ingredients of the composition and not deleterious to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be is "acceptable" in the sense of being compatible with the other ingredients of the formulation and not injurious to the subject. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prebiotic: As used herein, a "prebiotic" refers to an ingredient that allows or promotes specific changes, both in the composition and/or activity in the gastrointestinal microbiota that may (or may not) confer benefits upon the host. In some embodiments, a prebiotic can include one or more of the following: the prebiotic comprises a pome extract, berry extract and walnut extract.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. In some embodiments, prevention may be considered complete, for example, when onset of a disease, disorder or condition has been delayed for a predefined period of time.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is a negative control reference; in some embodiments, a reference is a positive control reference.

Risk: As will be understood from context, "risk" of a disease, disorder, and/or condition refers to a likelihood that a particular individual will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is 0, 1, 2, 3, 4, 5, 6, 7, 8, 9, 10, or more.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., bronchioalveolar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

Shelf-life: As used herein, the term "shelf-life" or "viable shelf-life" refers to the amount of time (expressed in days, months, or years) that a given composition comprises an amount of viable microbes (e.g., bacteria) that is above a minimum threshold of viable microbes required to produce a biological effect in a subject or group of subjects. Viability can be assessed by determining the ratio of live:dead cells in the composition at a given time, e.g., using an appropriate culture assay. In other embodiments, viability can be assessed functionally using a cell-based assay to measure the rate and/or maximal amount of ellagitannin hydrolysis by cells in a composition, formulation, or preparation. As will be appreciated by one of skill in the art, viability of a given composition is compared to a suitable reference, such as the viability of the composition on the day that it is packaged or a threshold rate/maximal amount of ellagitannins hydrolysis desired in the composition. As used herein the term "increased shelf-life" or "increased viable shelf-life" refers to an increase in the shelf-life of an ellagitannin composition (or composition or combination including an ellagitannin composition) by at least one day compared to a comparable composition. In other embodiments, an increased shelf-life refers to an increase of at least 2 days, at least 5 days, at least 7 days, at least 10 days, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months or more in an ellagitannin composition (or composition or combination including an ellagitannin composition) compared to a comparable composition. In some embodiments, a comparable composition lacks an ellagitannin.

Small molecule: As used herein, the term "small molecule" refers to small organic or inorganic molecules of molecular weight below about 3,000 Daltons. In general, small molecules may have a molecular weight of less than 3,000 Daltons (Da). Small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

Subject: As used herein, the term "subject" refers to an individual to which a provided treatment is administered. In some embodiments, a subject is animal. In some embodiments, a subject is a mammal, e.g., a mammal that experiences or is susceptible to a disease, disorder, or condition as described herein. In some embodiments, an animal is a vertebrate, e.g., a mammal, such as a non-human primate, (particularly a higher primate), a sheep, a dog, a rodent (e.g. a mouse or rat), a guinea pig, a goat, a pig, a cat, a rabbit, or a cow. Ins some embodiments, an animal is a non-mammal animal, such as a chicken, an amphibian, a reptile, or an invertebrate model *C. elegans*. In some embodiments, a subject is a human. In some embodiments, a patient is suffering from or susceptible to one or more diseases, disorders or conditions as described herein. In some embodiments, a patient displays one or more symptoms of a one or more diseases, disorders or conditions as described herein. In some embodiments, a patient has been diagnosed with one or more diseases, disorders or conditions as described herein. In some embodiments, the subject is receiving or has received certain therapy to diagnose and/or to treat a disease, disorder, or condition. In another embodiment, the subject is an experimental animal or animal substitute as a disease model.

Substantially: As used herein, refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Therapeutic regimen: A "therapeutic regimen", as that term is used herein, refers to a dosing regimen whose administration across a relevant population may be correlated with a desired or beneficial therapeutic outcome.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. It has been reported that the term "therapeutically effective amount" does not in fact require successful treatment be achieved in a particular subject. Rather, a therapeutically effective amount may be that amount that provides a particular desired pharmacological response in a significant number of subjects when administered to subjects in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). It has been reported that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively, or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

BRIEF DESCRIPTION OF THE DRAWING

FIG. 2, panel (B) includes a bar graph showing normalized expression levels from tannase (tan B), gallate decarboxylase (lpdB), and gallate decarboxylase (lpdC) genes in *C. elegans* fed negative control bacteria with (gray bars) and without (black bars) pome extract.

FIG. 3, panel (B) shows colony forming units of *L. plantarum* (MBT501) on a culture plate at 0, 2, and 4 weeks alone (black rectangle) or with pome extract (gray rectangle).

FIG. 4, panel (B) includes a Western blot showing Nrf2 protein levels in a human liver cell line (HepG) treated with *L. plantarum* (MBT501) alone, pome extract alone, or *L. plantarum* (MBT501) and pome extract.

DETAILED DESCRIPTION

Figure 1:
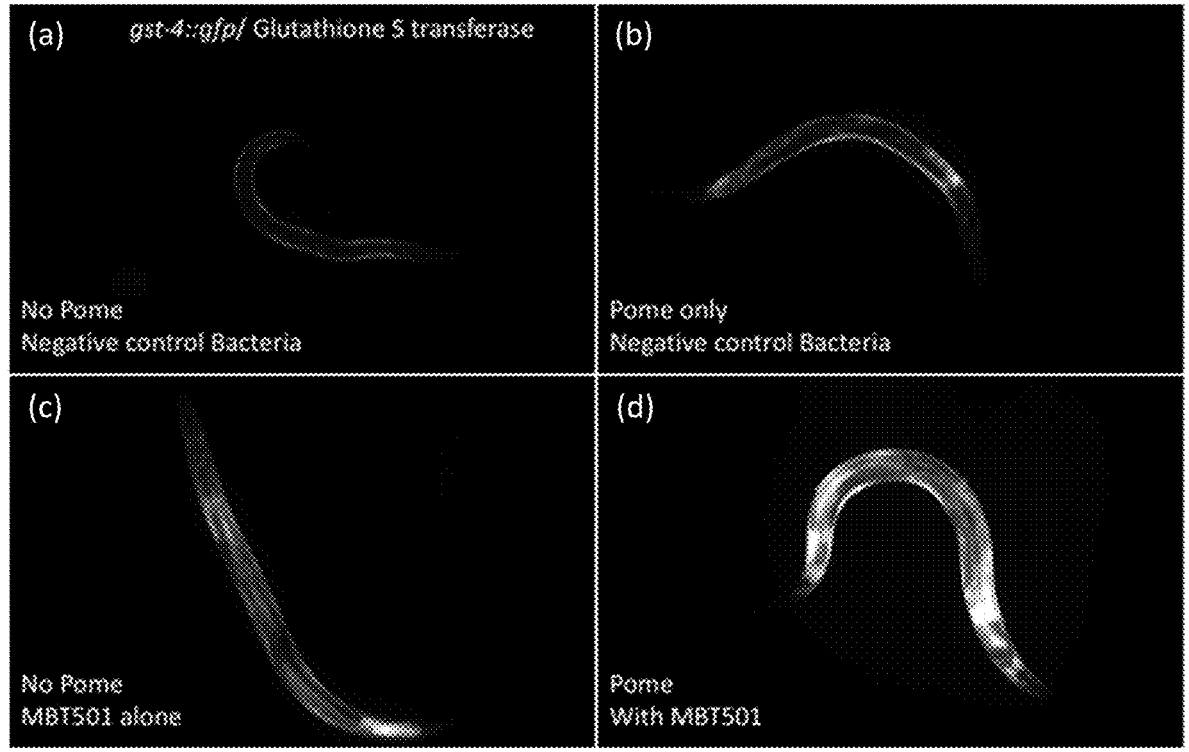
FIG. 1 shows induction levels of gst-4 expression using reporter CL2166 dvIs19 [pAF15 (gst-4::gfp-nls)] III in *Caenorhabditis elegans* using a qualitative visual screen. Panel (a) shows induction levels of gst-4 expression from the reporter CL2166 dvIs19 [pAF15 (gst-4::gfp-nls)] III in *C. elegans* fed negative control bacteria and no pome extract. Panel (b) shows induction levels of gst-4 expression from the reporter CL2166 dvIs19 [pAF15 (gst-4::gfp-nls)] III in *C. elegans* fed negative control bacteria and pome extract. Panel (c) shows induction levels of gst-4 expression from the reporter CL2166 dvIs19 [pAF15 (gst-4::gfp-nls)] III in *C. elegans* fed *Lactobacillus plantarum* (MBT501) and no pome extract. Panel (d) shows induction levels of gst-4 expression from the reporter CL2166 dvIs19 [pAF15 (gst-4::gfp-nls)] III in *C. elegans* fed *L. plantarum* (MBT501) and pome extract.

The present disclosure recognizes that ellagitannin metabolites have biological properties, including in some cases beneficial biological activities. For example, urolithins (e.g., urolithin A, urolithin B, urolithin C, urolithin D, and/or isourolithin A) resulting from ellagitannin metabolism may improve, e.g., mitochondrial function, by (among other things) increasing mitophagy (e.g., recycling of mitochondria by autophagy). While ellagitannin metabolites (e.g., urolithins) can influence biological activities, such metabolites have been reported to have a low bioavailability. Accordingly, a need for approaches that can increase the bioavailability of ellagitannin metabolites remains in the art.

The present disclosure provides the insight that enzymatic compositions comprising one or more ellagitannin enzymes (e.g., a tannin acyl hydrolase enzyme, a gallate decarboxylase enzyme, or a combination thereof) can be utilized to increase the bioavailability of urolithins resulting from the processing of ellagitannin. Thus, among other things, the present disclosure provides technologies in which one or more ellagitannin enzymes are included with an ellagitannin composition. Such technologies provide an increased production urolithins (e.g., urolithin A, urolithin B, urolithin C, urolithin D, and/or isourolithin A) and/or an increase in the bioavailability of urolithins (e.g., urolithin A, urolithin B, urolithin C, urolithin D, and/or isourolithin A), and therefore, provide a solution to needs in the art. In some embodiments, technologies herein can be useful for modifying (e.g., improving) mitochondrial function (e.g., by decreasing mitochondrial dysfunction), and/or modifying antioxidant levels.

The present disclosure provides the further insight that microbes, such as natural or genetically modified variants of microbial strains found in a microbiome (e.g., of a mammal, e.g., of a human), can include and/or express one or more ellagitannin enzymes (e.g., ellagitannin-enzyme-synthesizing microbes). Accordingly, the present disclosure provides, among other things, technologies that utilize such microbes, either alone or in combination with an ellagitannin composition, to increase production and/or bioavailability of urolithins. One benefit of using microbial strains that include and/or express one or more ellagitannin enzymes includes that microbial strains, such as those found in a microbiome, are generally safe for administration or consumption by a subject (e.g., a mammal, e.g., a human). Another benefit of using such microbial strains can be that microbial strains can colonize the gut of a subject to whom the strains are administered, which can reduce the number of administrations needed and lengthen the time in which ellagitannin enzymes are present in the gut of the subject. Additionally, microbial strains can be easy to administer to a subject via a number of probiotic forms, as discussed herein.

Ellagitannin Compositions

Ellagitannins are a diverse class of complex hydrolyzable plant tannin polyphenols composed of hexahydroxydiphenoyl moieties esterified to a sugar, i.e., hexahydroxydiphenoyl-glucose esters. Ellagitannins can be found in a variety of foods, such as strawberries (*Fragaria vesca*), raspberries, blackberries, cloudberries (*Rubus chamaemorus*), fruits of the Myrtaceae family, including, but not limited to jabuticaba, cambuci, Surinam cherries, camu-camu, red guava, white guava, pomegranate, walnuts, pecans, beefsteak fungus (*Fistulina hepatica*) and cranberries. Ellagitannin hexahydroxydiphenoyl-glucose esters may comprise varying numbers of hexahydroxydiphenoyl (HHDP) units and galloyl and/or sanguisorboyl units bound to a sugar, and may be produced primarily in dicot angiosperm plant species, including, but not limited to species in the order Myrtales.

Following consumption by a subject (e.g., a mammal, e.g., a human), ellagitannins (ETs) can be metabolized in the subject to ellagitannin metabolites, such as an ellagic acid (EA) metabolite, which can be, but is not limited to, urolithin A, urolithin B, urolithin C, urolithin D, isourolithin A, methyl-urolithin A, hydroxyl-urolithin A, and/or derivatives thereof. Although these metabolites can be derived from ellagitannins present in certain foods (e.g., pomegranates), the consumption of these foods often leads to insufficient bioavailability of these beneficial bioactive metabolites. Specifically, certain subjects may fail to produce detectable amounts of these metabolites after consumption of ET-containing foods (e.g., pomegranate juice). In some cases, subjects could benefit from compositions and methods described herein that can increase the bioavailability of ellagitannins in the diet and/or co-administered as part of a composition as described herein. Subjects who produce very low or undetectable levels of ellagitannin metabolites after ingestion may benefit from technologies disclosed herein. However, subjects who may produce detectable levels of ellagitannin metabolites can also benefit from technologies disclosed herein, as increased levels of such metabolites may be desirable.

In certain embodiments, an ellagitannin composition is used as a constituent of a composition described herein, or is administered in a method described herein. Non-limiting examples of ellagitannins useful in the methods and compositions described herein include pomegranate ellagitannins, which are numerous, but notably include punicalagins, including punicalin and gallagic acid, each of which can be hydrolyzed to ellagic acid (EA), which can be further hydrolyzed to urolithins A and B by gut microbes. Other ellagitannins include, for example, pedunculagins, rosacyanins (Fukiu et al., Tetrahedron 62: 9661-9670 (2006), which is incorporated herein by reference herein in its entirety), phyllanemblinins (Zhang et al., J. Nat. Prod. 64: 1527-1532 (2001), which is incorporated herein by reference) and sanguiin H6.

Ellagitannin compositions that may be useful in the methods and compositions described herein can include, for example, juices or homogenates of a plant material, including, but not limited to, fruit, or a peel and/or a husk thereof, of an ellagitannin-producing plant. It can be preferable to use a juice or homogenate enriched for ellagitannins by, for example, extraction. Different plant materials can be extracted in different ways. For example, in certain embodiments, materials can be extracted by solvent extraction of lyophilized, ground plant material. Some examples are discussed in the following.

An extraction of pomegranate husk or peel that can enrich for ellagitannins, while removing anthocyanins is described, e.g., by Adams et al., J. Agric. Food Chem. 54: 980-985 (2006), Seeram et al., Sep. Purif. Technol. 41: 49-55, and Sharma et al., J. Agric. Food Chem. 58: 3965-3969 (2010), each of which are incorporated herein by reference in their entirety. Purity and concentration of the ellagitannins in such extracts can be determined by HPLC and by liquid chromatography electrospray ionization mass spectrometry (LC-ESI/MS). Pomegranate extract can be obtained commercially, e.g., an extract comprising 37.5% of major pomegranate ellagitannins gallic acid, punicalagin and punicalagin, and 2.7% ellagic acid is available from Verdure Sciences, Noblesville Ind. That extract is prepared by the method described by Pacheco-Palencia et al., J. Agric. Food Chem. 56: 8434-8441 (2008), which is also incorporated herein by reference.

An extract of strawberry ellagitannins can be prepared as described, for example, by Zhang et al., J. Agric. Food Chem. 56: 670-675 (2008), which is also incorporated herein by reference. Briefly, lyophilized whole-fruit strawberry powder can be extracted by cold percolation with methanol to yield an extract that is then partitioned in chloroform followed by ethyl acetate. A remaining aqueous portion can be further purified by adsorption chromatography on an XAD-16 (Amberlite Resin, Sigma, St. Louis, Mo.) column and eluted with water followed by acidic methanol. Methanol eluate can be dried under vacuum and then further enriched in ellagitannin content by suspending in distilled water and filtering to yield a water insoluble fraction enriched in ellagitannins and ellagic acid. Extracts can be standardized by HPLC to 5.0% ellagic acid. Generally, resulting extracts can contain about 20.5% of phenolics, measured as gallic acid equivalents (GAEs).

A jamun seed extraction process is also described by Sharma et al., J. Agric. Food Chem. 58: 3965-3969 (2010), which is also incorporated herein by reference. Indian jamun (*Eugenia jambolana*) berry has ellagitannins in its fleshy pulp, but its seeds can be a richer source that do not contain as many anthocyanins. In some instances, anthocynanins can be removed. In some embodiments, compositions described herein are essentially free of or are free of anthocynanins. Extraction of jamun seeds can include, for example, extraction of seed powder in acetone, followed by vacuum drying. The resulting extract can be standardized by HPLC to about 4.2% ellagic acid, with 20.5% phenolics as GAEs. Similar approaches or others known previously can be applied to prepare ellagitannin-containing preparations from other sources for use in methods and compositions described herein.

An ellagitannin composition as disclosed herein can be formulated for oral administration. In some embodiments, an ellagitannin composition can be a food, a beverage, a feed composition, or a nutritional supplement. In some embodiments, an ellagitannin composition can be a liquid, syrup, tablet, troche, gummy, capsule, powder, gel, or film.

In some embodiments, an ellagitannin composition can be admixed with a pharmaceutically acceptable carrier. In some embodiments, an ellagitannin composition can be include in an enteric-coated formulation.

When consumed, ellagitannins can hydrolyze to release ellagic acid. Ellagic acid can be detected in human plasma and has been proposed to act directly on a methyltransferase involved in histone methylation, among other activities. However, ellagitannin metabolites, including, but not limited to, urolithin A (3,8-dihydroxyurolithin), urolithin C (3,8,9 trihydroxyuolithin), Isourolithin A (3,9 dihydroxyuolithin) urolithin B (3-hydroxyuolithin), urolithin D (3,4,8,9-tetrahydroxyurolithin) or a combination thereof require the action of gut microbiota on ellagitannins.

The concentration of urolithin A can reach up to micromolar (μM) levels in plasma without any apparent toxic effects in vivo. For example, upon consumption of pomegranate juice by humans, peak plasma levels of urolithin A can reach 14 to 40 μM. However, there may be wide variations among urolithin levels that result from ellagitannin processing among individuals (see, e.g., Cerda et al., Eur. J. Nut. 43: 205-220, which is incorporated herein by reference). Selma et al. identified mono-cultured bacteria (*Gordonibacter* urolithinfaciens and *Gordonibacter pamelaeae* DSM 19378T) that can metabolize ellagic acid to produce luteic acid, urolithin M-5, urolithin M-6 and urolithin C. However, these cultured bacteria were incapable of producing downstream products, urolithin A and urolithin B; see Selma et al., Food & Nut. 5: 1779-1784 (2014), which is incorporated herein by reference. The present disclosure provides the recognition that wide inter-individual variation may be due to differences in microbiota.

Tissue disposition studies reveal that urolithins may be enriched in prostate, intestinal, and colon tissues in mouse. Urolithin A can inhibit proliferation of colon cancer cells, induce cell cycle arrest, and modulate key cellular processes associated with colon cancer development, such as MAPK signaling in vitro (Larossa et al, J. Agric. Fool Chem., 54: 1611-1620 (2006); Gonzalez-Sarrias et al., Mol. Nut. Food Res. 53: 686-698 (2009), each of which is incorporated herein by reference). In a rat colitis model, urolithin A can decrease inflammatory markers including inducible nitric oxide synthase, cycloxygenase-2 (COX-2), prostaglandin E synthase and prostaglandin E2, in colonic mucosa. Urolithin B has been found to be a regulator of skeletal muscle mass in some embodiments (see, e.g., Rodriguez et al., J. Cachexia Sarcopenia Muscle 8: 583-597 (2017), which is incorporated herein by reference). Where urolithins are directly bioavailable, treatments that promote urolithin production as described herein can increase the bioavailability of ellagitannin metabolites.

Urolithins have distinct UV spectra that can permit their detection and measurement by, for example, HPLC coupled with UV photodiode array detectors. Correlations between structural characteristics, including conjugation, with the UV spectra and retention times have been reported (see, e.g., Gonzalez-Barrio et al., J. Agric. Food Chem. 59: 1152-1162 (2011), which is incorporated herein by reference). Thus, HPLC and UHPLC can be used to assay and identify levels of urolithins in urine obtained from a subject (see e.g., Piwowarski, J P et al. Drug Metabolism and Disposition 45(6):657-665 (2017), the contents of which are incorporated herein by reference in its entirety).

Ellagitannin Enzymes
Tannin Acyl Hydrolase Enzymes

Embodiments of the compositions and methods described herein include use of microbes that express enzymes that act on ellagitannins or in an ellagitannin metabolic pathway. Exemplary enzymes include tannin acyl hydrolase enzymes that can catalyze hydrolysis of the galloyl ester bond in hydrolysable tannins, including ellagitannins, to release gallic acid. Tannin acyl hydrolases as described herein can catalyze a reaction characteristic of E.C. 3.1.1.20. Fungi, such as *Aspergillus* species, and bacteria, such as members of the family Lactobacillaceae, can naturally produce tannase enzymes suitable for use in compositions and methods as described herein. Tannase enzymes encoded by fungi may share little structural similarity to those encoded by bacteria, yet they can share a similar range of substrate specificities. As such, for embodiments in which tannase enzyme can be administered or used as a preparation derived from, but not including, live microorganisms, tannase can be isolated or prepared from fungal, as well as bacterial sources. Tannases produced by yeast and methods of producing them are described, for example, by Boer et al., Yeast 26: 323-337 (2009), and secretion, purification and characterization of *Aspergillus oryzae* tannase in Pichjia *pastoris* yeast is described by Zhong et al., Protein Expression and Purif. 36: 165-169 (2004), both of which are incorporated herein by reference.

Tannases acting on ellagitannins can selectively hydrolyze galloyl moieties, yielding gallic acid and degalloylated ellagitannins. See, e.g., Rodriguez-Duran et al., Enzyme Res. 2011: 823619 (2011), which includes illustrations of hydrolytic products of tannase digestion of various ellagitannins, and is incorporated herein by reference. In one embodiment, a tannin acyl hydrolase is a tannase B or tan B tannase enzyme. Examples include, but are not limited to, tan B enzymes encoded and expressed by members of the Lactobacillaceae family, including, but not limited to, *L. plantarum* species. Tannase B tannases encoded and expressed by other species that can catalyze the same reaction may also be useful in various embodiments of the compositions and methods described herein, as can naturally-occurring or artificially created variants that retain the ability to catalyze the same reaction.

Methods of producing and isolating recombinant tannase, for example, *L. plantarum* tannase, are described, for example, by Curiel et al., J. Agric. Food Chem. 57: 6224-6230 (2009), which is incorporated herein by reference. The crystal structure of a tannase B polypeptide encoded and expressed by *L. plantarum* has been determined (see Ren et al., J. Mol. Biol. 425: 2737-2751 (2013), which is incorporated herein by reference). As reported, tannase B displays an α/β structure, featured by a large cap domain inserted into a serine hydrolase fold. Structural studies of the enzyme in complex with a number of substrates indicated that the interactions at a galloyl binding site are a determinant force for the binding of substrates. A galloyl binding site is responsible for esterase and depsidase activities of the enzyme. A catalytic triad composed of Ser163, His451, and Asp419 was identified. Mutagenesis studies showed that during binding of gallic acid, the carboxyl group of the molecule forges hydrogen-bonding interactions with the catalytic triad of the enzyme, while the three hydroxyl groups make contacts with Asp421, Lys343, and Glu357 to form another hydrogen-bonding network, and that these residues are necessary for enzyme activity. As such, modifications to tannin acyl hydrolase or tannase B polypeptide that change the identity of one or more of these residues or their equivalent in homologous proteins will likely not be tolerated. Similarly, it is anticipated that changes that disrupt the positioning of these residues or their equivalent in other homologues relative to each other would also disrupt hydrogen bonding networks and interfere with enzyme function. On the other hand, changes that do not affect the identity or relative positioning of the noted residues would be more likely to be tolerated. In one embodiment, a tannase B polypeptide as described herein is at least 85% identical to a *L. plantarum* tannase B enzyme encoded by strain WCFS1 and retains catalytic triad amino acids Ser163, His451 and Asp419 and tannin hydroxyl-contacting amino acids Asp 421, Lys343 and Glu357 noted above, or their equivalent as located in homologous polypeptides. In another embodiment, a tannase B polypeptide as described herein has at least 90% or at least 95% or greater identity to a *L. plantarum* tannase B enzyme encoded by strain WCFS1 and retains the catalytic triad amino acids Ser163, His451 and Asp419 and tannin hydroxyl-contacting amino acids Asp 421, Lys343 and Glu357 noted above, or their equivalent as located in homologous polypeptides.

A large number of *L. plantarum* strains encode and express a similar tannase B polypeptide. Non-limiting examples include, *L. plantarum* WCFS1 (see, nucleic acid and amino acid sequences below), as well as, for example, *L. plantarum* 5-2, *L. plantarum* LP3, *L. plantarum* BLS41, *L. plantarum* LQ80, *L. plantarum* A3, *L. plantarum* FBR6, and *L. plantarum* RI-515.

*L. plantarum* WCFS1 tannase B nucleic acid sequence (NCBI Accession No. NC_004567.2):

```
atgagtaacc gattgatttt tgatgctgac tggctggtgc cggaacaggt ccaagttgcc gggcaggcta ttcaatatta
```

```
tgctgcccgt aatattcagt acgttcagca tccagtcgca gcgattcagg tcctaaacgt ttttgtacca gccgcatact tgcatggcag ttcagtcaat ggttatcagc gggcaacggc gccaattctg atgccgaata cggtcggcgg ttatttgcca ggaccggcgg atgatccgca acgtgtcact tggccgacga atgcagggac gattcaacag gcacttaaac gcggttacgt tgtggtggcc gctggaattc gcggtcgtac gacggttgat aagtctgggc aacgggtcgg gcaagcgccg gcttttatcg ggcggcaatc cgttacgtta agtataatca gggccggctg ccaggtgaca cgaaccggat catcacgaat ggaacgagtg tagatatgaa ctgggggtgc cacttcggct ttagcgggtg cgagtggcaa ttcggcttat tttgaaccag ccttaactgc gctcggggca gcaccggcga ctgacgatat ctttgcggtg tcagcttact gcccgattca taatctggaa cacgcagaca tggcctacga gtggcagttt aatggtatta atgactggca ccgttatcag cctgttgcgg ggacgaccaa gaatgggcga ccaaaatttg aaccggttag tggtcagctc acagttgaag aacaggccct ttcgttggcg ttaaaagccc agttcagtac ctacttgaac cagttgaaac tcacggccag tgacgggacg cacttgacgc ttaatgaggc gggaatgggt tcatttcgtg atgttgttcg ccaattattg atatcatctg ctcagacggc attcgatcaa gggacggata ttcataagta cgcaggcttt gtcgttactg gaaatcaggt gacggacttg gatttatcag cttatttgaa gtcgttaact cgcatgaaag ccgtcccggc gtttgaccaa ttagatttga cgagtccaga gaataatttg tttggcgatg caacggcgaa agccaagcac tttacggcct tggcacagac gcgaagtacg gtgacggcac aactagcgga cgctgagctg attcaggcga ttaatccgct cagttactta acgacaactt cgtcacgagt tgctaagcac tggcggattc gccacggtgc ggccgaccga gatacgagtt ttgcaatccc gattattcta gcaataatgt tagaaaatca tggttatggc attgattttg cgctaccgtg ggatattccc cacagtggtg actatgattt aggcgattta ttttcctgga ttgatggctt gtgccaatga
```

L. plantarum WCFS1 tannase B amino acid sequence, NCBI Accession No. WP_011101979.1:

```
MSNRLIFDAD WLVPEQVQVA GQAIQYYAAR NIQYVQHPVA

AIQVLNVFVP AAYLHGSSVN GYQRATAPIL MPNTVGGYLP

GPADDPQRVT WPTNAGTIQQ ALKRGYVVVA AGIRGRTTVD

KSGQRVGQAP AFIVDMKAAI RYVKYNQGRL PGDTNRIITN

GTSAGGATSA LAGASGNSAY FEPALTALGA APATDDIFAV

SAYCPIHNLE HADMAYEWQF NGINDWHRYQ PVAGTTKNGR

PKFEPVSGQL TVEEQALSLA LKAQFSTYLN QLKLTASDGT

HLTLNEAGMG SFRDVVRQLL ISSAQTAFDQ GTDIHKYAGF

VVTGNQVTDL DLSAYLKSLT RMKAVPAFDQ LDLTSPENNL

FGDATAKAKH FTALAQTRST VTAQLADAEL IQAINPLSYL

TTTSSRVAKH WRIRHGAADR DTSFAIPIIL AIMLENHGYG

IDFALPWDIP HSGDYDLGDL FSWIDGLCQ
```

Amino acids Ser163, His451, Asp419, Asp 421, Lys343 and Glu357 are bolded.

Methods for detecting or measuring tannin acyl hydrolase activity include exemplary methods such as those described by: Beverini & Metche, Sci. Aliments. 10: 807-816 (1990) describing an HPLC assay, Haslam et al. J. Chem. Soc. 1829-1835 (1961) describing an unbuffered titrimetric assay, Yamada et al. Agr. Biol. Chem. 45: 233-240 (1967) describing a buffered titrimetric assay, Skene & Booker, Anareobe 1: 321-327 (1995) describing a single wavelength spectrophotometric assay, Bajpai & Patil, World J. Microbiol. Biotechnol. 12: 217-220 (1996) describing a double-wavelength spectrophotometric assay, and Aguilar et al. (Braz. Arch. Biol. Technol. 42 (No. 3), Curitiba 1999) describing a double-wavelength spectrophotometric assay. Each of these publications is incorporated herein by reference in its entirety, and particularly with respect to tannin acyl hydrolase assay conditions and calculation of results. The Aguilar reference includes a comparison of these six methods, using tannic acid as the sole substrate in the enzymatic reaction. Each of the methods described were useful for measuring extracellular tannin acyl hydrolase activity, and all except the Bajpai & Patil method were useful for measurement of intracellular activity. For spectrophotometric and HPLC assays, one unit of enzyme activity is typically defined as an amount of enzyme liberating 1 μmol (micromole) of gallic acid per ml per minute; for the titrimetric methods, one unit of enzyme is typically an amount of enzyme that releases 1 μmol carboxyl group per ml per minute. While any of these methods can be used on the basis of this comparison, the HPLC assay described by Beverini and Metche had the lowest coefficient of variation, indicating a higher reliability than other methods. An HPLC method can be preferred when accuracy in measuring tannin acyl hydrolase activity matters. To determine whether a given bacterium expresses a tannin acyl hydrolase activity, any of the assays provided above, among others, can be used, but where necessary or desired to measure the amount of such activity, a HPLC approach is preferred. The presence of a tannin acyl hydrolase gene can be detected in a bacterium via PCR using primers based on available tannin acyl hydrolase nucleic acid sequences, or, where the genome of the bacterium has been sequenced, the presence of sequence encoding a tannin acyl hydrolase can be determined based upon homology or identity to known tannin acyl hydrolases.

Gallate Decarboxylase Enzymes

Embodiments of the compositions and methods described herein include the use of microbes that encode and express a gallate decarboxylase enzyme. The enzyme can catalyze the conversion of 3,4,5-trihydroxybenzoate (gallic acid) to pyrogallol and carbon dioxide, which is a characteristic of E.C. 4.1.1.59. Microbial gallate decarboxylase genes can be encoded in an operon arrangement of three separate protein coding sequences referred to as "subunits" C, B and D, but an active enzyme is not a complex of the three subunits. Rather, for species that have this arrangement, the C subunit appears to be the catalytic subunit. In *Lactobacillus plantarum* WCFS1, a B subunit, but not a D subunit is required together with a C subunit for gallate decarboxylase activity, based on gene knockout experiments; it has been proposed that the B subunit plays a role in, for example, establishing correct folding of the C subunit. See, e.g., Jimenez et al., Appl. Environ. Microbiol. 79: 4253-4263 (2013), which is incorporated herein by reference. For the gallate decarboxylase expressed by *L. plantarum* WCFS1 (also known as ATCC-deposited strain BAA-793), the C subunit, lpdC, has the sequence at GenBank Accession No. F9US27-1:

```
atggcagaac aaccatggga tttgcgtcgc gtgcttgatg
agatcaagga tgatccaaag aactatcatg aaactgacgt
cgaagttgat ccaaatgcgg aactttctgg tgtttatcgg
tatatcggtg ctggtgggac cgttcaacgg ccaacgcaag
agggtccagc aatgatgttt aacaacgtta aggggtttcc
tgatacgcgg gtcttgactg gattgatggc gagtcgccgg
cgcgttggta agatgttcca ccacgattat cagacgttag
ggcaatactt gaacgaagca gtctctaatc cagtggcgcc
agaaacggtt gctgaagcgg atgcgccagc tcacgatgtc
gtttataaag cgacggatga aggctttgat attcgtaagt
tagtggcagc accaacgaat acgcccaag atgctggacc
atatattacg gtcggtgtgg tgtttggctc aagcatggac
aagtctaaga gtgatgtgac gattcaccga atggtccttg
aagataagga taagttaggg atttatatca tgcctggcgg
tcggcacatt ggtgcgtttg cggaagagta tgagaaagct
aacaagccaa tgccaattac aattaatatt ggtttggatc
cagccattac gattggtgca actttcgaac caccgaccac
gccattcggt tataacgaat taggtgttgc tggtgcgatt
cggaaccaag ctgttcaatt agttgacggg gtgaccgtcg
atgaaaaggc gattgcgcgt tctgaatata cgcttgaggg
gtacattatg cctaacgaac gtattcagga agatatcaat
acgcatacgg gcaaggcgat gcctgaattc ccgggttatg
atggtgacgc caacccagct ttacaagtga ttaaggtgac
ggcggtgact catcggaaga atgccatcat gcaaagcgtg
attggaccat ccgaagaaca tgtcagcatg gcgggaattc
caactgaagc tagtatctta caattggtta accgtgccat
tcctggtaaa gtgacgaatg tttataatcc gccggctggt
ggtggtaagt tgatgaccat catgcagatt cacaaggata
atgaagcgga tgaaggaatt caacggcaag ctgccttgct
tgcgttctca gcctttaagg aattgaagac tgttatcctg
gttgatgaag atgttgatat ttttgatatg aatgatgtga
tttggacgat gaatacccgt ttccaagccg atcaggactt
gatggtctta tcaggcatgc ggaatcatcc gttggaccca
tcggaacgcc cacaatatga tccaaagtcg attcgtttcc
gtgggatgag ttctaaacta gtgattgatg gcaccgtacc
attcgatatg aaggaccaat tgaacgggc ccaattcatg
aaagtggctg actgggagaa gtatttgaag taa
``` lpdC:
F9US27-1 (UniprotKB; *L. plantarum* ATCC BAA-793)

```
MAEQPWDLRR VLDEIKDDPK NYHETDVEVD PNAELSGVYR
YIGAGGTVQR PTQEGPAMMF NNVKGFPDTR VLTGLMASRR
RVGKMFHHDY QTLGQYLNEA VSNPVAPETV AEADAPAHDV
VYKATDEGFD IRKLVAAPTN TPQDAGPYIT VGVVFGSSMD
KSKSDVTIHR MVLEDKDKLG IYIMPGGRHI GAFAEEYEKA
NKPMPITINI GLDPAITIGA TFEPPTTPFG YNELGVAGAI
RNQAVQLVDG VTVDEKAIAR SEYTLEGYIM PNERIQEDIN
THTGKAMPEF PGYDGDANPA LQVIKVTAVT HRKNAIMQSV
IGPSEEHVSM AGIPTEASIL QLVNRAIPGK VTNVYNPPAG
GGKLMTIMQI HKDNEADEGI QRQAALLAFS AFKELKTVIL
VDEDVDIFDM NDVIWTMNTR FQADQDLMVL SGMRNHPLDP
SERPQYDPKS IRFRGMSSKL VIDGTVPFDM KDQFERAQFM
KVADWEKYLK
```

The B subunit of the *L. plantarum* WCFS1 gallate decarboxylase (lpdB) has the sequence at GenBank Accession No. F9UT67:

```
atgaaacgaa ttgttgtggg aatcacggga gcgtccggta
cgatttacgc ggtcgactta ttagaaaagt tacatcagcg
gccagatgtt gaagttcatc tggtaatgag tgcgtgggct
aaaaaaaact tggagttaga gactgattac tcgctcgcgc
agctgacggc gctcgcggat gctacttatc gggctaatga
ccaaggcgca gcgattgcca gcggttcgtt tttgaatgac
ggaatggtca ttgtcccagc tagtatgaag acggtagcag
ggattgcgta cggcttcggt gataatttaa tatcgcgggc
tgctgatgtc acgattaaag aacaacgtaa acttgtgatt
gttccacgtg aaacaccgtt aagcgtgatt catttagaaa
atctaacgaa gttggcaaaa ctcggtgccc aaattattcc
accgattccc gcgtttata atcatccgca atccattcag
gatctggtca atcatcaaac catgaaaatt ttagatgcgt
ttcatattca taatgaaact gatcgccgtt gggaggggga
taa
MKRIVVGITG ASGTIYAVDL LEKLHQRPDV EVHLVMSAWA
```

```
KKNLELETDY SLAQLTALAD ATYRANDQGA AIASGSFLND

GMVIVPASMK TVAGIAYGFG DNLISRAADV TIKEQRKLVI

VPRETPLSVI HLENLTKLAK LGAQIIPPIP AFYNHPQSIQ

DLVNHQTMKI LDAFHIHNET DRRWEGD
```

The D subunit of, for example, *L. plantarum* gallate decarboxylase (lpdD) has the sequence at GenBank Accession No. F9UT68:

```
atggcaactt ttacgactga gcaggccggg tatcaaatgc aagcaatact ccaagtgatt ggatatgact tgttgatcgt cgttaccggt gggaccaatc cccatattgg tgacgtgacc acactaactg ccagcacggt tcccgaaacg gttaagtttc ccagccatga tggtcgcttc cacaaagata actttatttc ggaacgaatg gccaagcgga ttcagcgtta tctagctgga agctgtacaa ttactgcggg aattcatgtc aaccaaatta ctaaagcaca aatagcagct gcggcaccaa tgacggatga cctcagccgc cagattatta gctggttaca ggcccatccc gtccaggctg aaaagccgga atattatgga caagacgagc aaccgcggta g

MATFTTEQAG YQMQAILQVI GYDLLIVVTG GTNPHIGDVT

TLTASTVPET VKFPSHDGRF HKDNFISERM AKRIQRYLAG

SCTITAGIHV NQITKAQIAA AAPMTDDLSR QIISWLQAHP

VQAEKPEYYG QDEQPR
```

In *L. plantarum* species that express gallate decarboxylase, and other species that express gallate decarboxylase, such as *Streptococcus* galloylyticus, gallic acid released from tannins, e.g., by action of tannin acyl hydrolase enzymes, can be decarboxylated to pyrogallol, but these species lack the ability to further degrade this product. Gallate decarboxylase enzymes from a number of microbial sources are known, including, but not limited to *Lactobacillus plantarum*, e.g., *L. plantarum* WCFS1. Gallate decarboxylase activity is widely present among lactic acid bacteria, e.g., *L. brevis, L. casei* and *L. fermentum*.

In one embodiment, the gallate decarboxylase comprises a gallate decarboxylase C polypeptide, such as, but not limited to an *L. plantarum* lpdC polypeptide. In another embodiment, a microbe useful in methods and compositions described herein encodes and expresses gallate decarboxylase C and B polypeptides. In such microbes or compositions made from or comprising them, the B polypeptide is not necessarily bound to the C polypeptide, but appears to be important for generating highly active gallate decarboxylase enzyme. Examples include, but are not limited to lpdC and lpdB polypeptides of *L. plantarum* species, including but not limited to *L. plantarum* WCFS1, among others. Gallate decarboxylases encoded and expressed by other species and that catalyze the same reaction can also be useful in various embodiments of the compositions and methods described herein, as can naturally-occurring or artificially created variants that retain the ability to catalyze the same reaction.

Methods of expressing or producing recombinant gallate decarboxylase are similar to those for producing recombinant tannin acyl hydrolase enzymes or other recombinant enzyme preparations. See, e.g., Jimenez et al., Appl. Environ. Microbiol. 79: 4253-4263 (2013), which is incorporated herein by reference. Gallate decarboxylase activity can be assayed as described therein as well, and the authors further describe PCR primers and PCR amplification to identify species that encode enzyme activity and to prepare nucleic acids encoding enzyme polypeptides, e.g., for cloning into expression vectors for overexpression.

In one embodiment, a gallate decarboxylase enzyme has at least 80% sequence identity to the catalytic gallate decarboxylase C polypeptide of *L. plantarum* lpdC of strain WCFS1 as described herein and retains at least 50% of the gallate decarboxylase activity of the lpdC polypeptide when expressed in the presence of lpdB polypeptide. Variations contemplated in a gallate decarboxylase enzyme molecule include, for example, conservative amino acid substitutions as the term is defined herein Thus, in one embodiment, a gallate decarboxylase enzyme has 50 or fewer, e.g., 40 or fewer, 30 or fewer, 20 or fewer, 15 or fewer, 10 or fewer, 5 or fewer, 4 or fewer, 3 or fewer, 2 or fewer or one or fewer conservative amino acid substitutions relative to a wild-type gallate decarboxylase enzyme, or relative to a gallate decarboxylase enzyme encoded and expressed by *L. plantarum* WCFS1, and retains at least 50%, at least 60%, at least 70%, at least 80%, at least 90%, at least 95%, at least 96%, at least 97%, at least 98%, at least 99% or higher activity relative to a wild type enzyme or that encoded and expressed by *L. plantarum* WCFS1. In another embodiment, a gallate decarboxylase enzyme has at least 80%, at least 85%, at least 90%, at least 95%, at least 96%, at least 97%, at least 98%, at least 99% or greater sequence identity to a catalytic gallate decarboxylase C polypeptide of *L. plantarum* lpdC of strain WCFS1 as described herein and retains at least 50%, at least 60%, at least 70%, at least 80%, at least 90%, at least 95%, at least 96%, at least 97%, at least 98%, at least 99% or more of the gallate decarboxylase activity of a lpdC polypeptide when expressed in the presence of a lpdB polypeptide. It is contemplated that some mutations can potentially improve the relevant activity, such that a gallate decarboxylase variant has more than 100% of the activity of a wild-type or native polypeptide, e.g., 110%, 125%, 150%, 175%, 200%, 500%, 1000% or more.

Ellagitannin-Enzyme-Synthesizing (EES) Microbes

A number of microbial species are known that encode and can produce tannase enzymes as described herein, as are species that encode and can produce gallate decarboxylase as described herein. In one embodiment, a single microbial species or strain can express both tannase and gallate decarboxylase enzymes. In another embodiment, each enzyme is encoded and can be expressed by a different species or strain; in such instances it is generally beneficial to administer both species or strains to provide the best benefit in terms of ellagitannins metabolism and urolithin production. In addition to microbes that can natively express tannase and/or gallate decarboxylase enzymes, microbes can be engineered to recombinantly express enzymes of interest. In one embodiment, a microbial species or strain may be modified such that both tannase and gallate decarboxylase enzymes can be engineered to include a polynucleotide that encodes the enzymes and thus can be recombinantly expressed. In another embodiment, a microbial species or strain may be modified such that either tannase or gallate decarboxylase enzymes are encoded and can be recombinantly expressed.

It is possible to identify a species or strain of microbes that encodes a given enzyme or enzyme gene cluster using, e.g., genomic sequencing. Once a species or strain is identified as encoding a given enzyme or enzyme gene cluster, it can be determined whether the bacterium actually produces the enzyme(s) using transcriptomics, RT-PCR, or analysis of expressed proteins via Western blot or other antibody-based assay or via an assay for enzyme activity that was known previously.

*Lactobacillus plantarum* is an exemplary species that encodes and can express tannase and gallate decarboxylase enzymes. In some embodiments, *Streptococcus gallolyticus* is used (Genetic and biochemical approaches towards unravelling the degradation of gallotannins by *Streptococcus gallolyticus*, Microb Cell Fact. 2014 Oct. 31; 13:154. doi: 10.1186/s12934-014-0154-8, which is incorporated herein by reference).

Combinations

Given that certain factors can influence the effective amount of ellagitannin composition and effective amount of microbes that encode and can express tannin acyl hydrolase and gallate decarboxylase enzymes, it should also be understood that various combinations of ellagitannin amount and microbes amount can provide an amount effective to promote urolithin production in the gut as described herein. Thus, for example, a combination can include an ellagitannin composition, and an enzymatic composition comprising one or more ellagitannin enzymes. In some embodiments, one or more ellagitannin enzymes comprise a tannin acyl hydrolase enzyme, a gallate decarboxylase enzyme, or a combination thereof. In some embodiments, an enzymatic composition can be an EES microbe.

In some embodiments, a combination can include about 10 mg to about 10 g, about 10 mg to about 5 g, 10 mg to about 2500 mg, about 100 mg to about 10 g, about 100 mg to about 5 g, or 100 mg to about 2500 mg of an ellagitannin composition. In some embodiments, a combination can include at least 10 mg, at least 50 mg, at least 100 mg, at least 150 mg, at least 200 mg, at least 250 mg, at least 300 mg, at least 350 mg, at least 400 mg, at least 450 mg, at least 500 mg, at least 550 mg, at least 600 mg, at least 650 mg, at least 700 mg, at least 800 mg, at least 850 mg, at least 900 mg, at least 950 mg, at least 1000 mg (1 g), at least 1250 mg, at least 1500 mg, at least 2000 mg, at least 2500 mg, at least 3000 mg, at least 3500 mg, at least 4000 mg, at least 4500 mg, at least 5000 mg, or more of an ellagitannin composition. In some embodiments, a combination can include at most 50 mg, at most 100 mg, at most 150 mg, at most 200 mg, at most 250 mg, at most 300 mg, at most 350 mg, at most 400 mg, at most 450 mg, at most 500 mg, at most 550 mg, at most 600 mg, at most 650 mg, at most 700 mg, at most 800 mg, at most 850 mg, at most 900 mg, at most 950 mg, at most 1000 mg (1 g), at most 1250 mg, at most 1500 mg, at most 2000 mg, at most 2500 mg, at most 3000 mg, at most 3500 mg, at most 4000 mg, at most 4500 mg, at most 5000 mg, at most 5500 mg, at most 6000 mg, at most 6500 mg, at most 7000 mg, at most 7500 mg, at most 8000 mg, at most 8500 mg, at most 9000 mg, at most 9500 mg, or at most 10 g of an ellagitannin composition.

In some embodiments, a composition can include about $10^5$ CFU to $10^{12}$ CFU, about $10^5$ CFU to $10^{10}$ CFU, or about $10^8$ CFU to $10^{12}$ CFU of one or more EES microbes. In some embodiments, a composition can include at least $10^5$, $5\times10^5$, $10^6$, $5\times10^6$, $10^7$, $5\times10^7$, $10^8$, $5\times10^8$, $10^9$, $5\times10^9$, $10^{10}$, $5\times10^{10}$, $10^{11}$, $5\times10^{11}$, $10^{12}$, or more of one or more EES microbes.

The amount of an ellagitannin composition effective to promote urolithin production will vary with, for example, the amount and/or activity of microbes in the gut that can metabolize ellagitannins. Thus, when an ellagitannin composition is consumed or administered with a preparation or formulation comprising microbes that encode and express tannin acyl hydrolase and/or gallate decarboxylase enzymes, the amount of ellagitannin composition effective to promote urolithin production will generally be lower than a case where ellagitannins are consumed or administered without such microbes. It should be understood that where the enzyme expression levels from microbes that encode and express tannin acyl hydrolase and/or gallate decarboxylase enzymes can vary, the amount of microbes necessary to promote urolithin production will vary with such expression levels; that is, the amount of a given microbial strain or strains can be adjusted for effect depending upon relative levels of tannin acyl hydrolase and/or gallate decarboxylase enzymes that are produced. It should also be noted that the presence of ellagitannins can induce expression of enzymes necessary to metabolize them in microbes that can encode such enzymes—see, e.g., Example 2. Thus, when microbes are or have recently been exposed to ellagitannins, an amount of microbes necessary to promote urolithin production may be lower than an amount needed when the microbes have not been so exposed prior to administration or consumption.

In one embodiment, effective treatment can be determined by an increase in urolithin concentration in excreted urine by at least 10%, at least 20%, at least 30%, at least 40%, or at least 50% compared to the level of urinary urolithin prior to treatment with a composition comprising an ellagitannin composition or an ellagitannin composition in combination with microbes that encode and express a tannin acyl hydrolase and/or a gallate decarboxylase as described herein. In some embodiments, efficacy can be assessed by measuring the degree of oxidative stress of cells in a biological sample prior to and following administration of a composition as described herein. The degree of oxidative stress of cells can be assessed by, for example, measuring the expression of oxidative stress biomarkers, such as high sensitivity C-reactive protein (hs-CRP) or by determining the ratio of oxidized to reduced forms of glutathione. High levels of oxidative stress can be cytotoxic, so the degree of oxidative stress can be measured by assessing the concentration of intracellular proteins present in the systemic circulation from inflamed or lysed cells, for example, cardiomyocyte oxidative stress can be determined by assessing troponin-I levels in blood. Liver oxidative stress can be determined by the presence of increased levels of liver enzymes in the bloodstream, including, but not limited to, alanine transaminase (ALT), aspartate transaminase (AST), alkaline phosphatase (ALP) and gamma-glutamyl transpeptidase (GGT).

In some embodiments, effective treatment can be determined by an increase in urolithin concentration in the gut of a subject by at least 10%, at least 20%, at least 30%, at least 40%, or at least 50% compared to the level of urolithin in the gut prior to treatment with a composition comprising an ellagitannin composition or an ellagitannin composition in combination with microbes that encode and express a tannin acyl hydrolase and/or a gallate decarboxylase as described herein. In some embodiments, effective treatment can be determined by an increase in urolithin concentration in plasma of a subject by at least 10%, at least 20%, at least 30%, at least 40%, or at least 50% compared to the plasma level of urolithin prior to treatment with a composition comprising an ellagitannin composition or an ellagitannin composition in combination with microbes that encode and express a tannin acyl hydrolase and/or a gallate decarboxylase as described herein.

In some embodiments, a subject is evaluated using one or more additional diagnostic procedures, for example, by medical imaging, physical exam, laboratory test(s), clinical history, family history, and genetic test. Medical imaging techniques are well-documented methods. As such, medical imaging can be selected from any known method of imaging, including, but not limited to, ultrasound, computed tomography scan, positron emission tomography, photon emission computerized tomography, and magnetic resonance imaging.

Bioavailability of an Ellagitannin Composition

Phenolic compounds constitute a substantial and an important group of phenylpropanoids produced by plants as secondary metabolites for the purpose of chemical defense against predators and to participate in reproduction as well as in plant-plant interference. Structurally, phenolic compounds have an aromatic ring with several hydroxyl groups attached to it. Phenolic compounds are classified into different groups based on their function, the number of phenolic rings that they contain, and the radicals that bind these rings to another one. An important factor in the determination of antioxidant activity of a given phenolic compound is both the number and position of hydroxyl groups. For example, flavonoids have more hydroxyl groups than other phenolic compounds and this structure is associated with higher antioxidant activity. In addition to providing antioxidant activity, the structure of a phenolic compound can affect the solubility of the phenol and/or impart steric effects regarding interaction with other molecules.

It has been reported that the structure of such compounds can play a role in their bioavailability. Whether a compound is bioavailable depends on the formulation, the absorption characteristics, gastric emptying rate, the route of administration, degradation and elimination kinetics in a given subject. Thus, bioavailability of a compound can vary from one individual to the next. Bioavailability can be assessed using an assay to measure levels of a given compound in the systemic circulation, and in particular, in blood, plasma, and/or urine.

Another important determinant of bioavailability is "bioaccessibility," which relates to the amount of a food constituent, nutrient (e.g., polyphenols) etc. that is released from the food matrix into the gut and can be absorbed through the intestinal barrier. Bioaccessibility relates to the degree in which a food is masticated, whether the food is cooked or raw, gastric emptying time, gut transit time, the amount of fiber or fat in the food, what is consumed alongside the food, cofactors necessary for absorption, presence of particular microorganisms, and the complexity of the food matrix structure.

A bioavailable compound may not be bioactive simply because it is absorbed. For example, some nutrients are not directly active and require metabolism to a bioactive metabolite. Further, some polyphenols are high molecular weight compounds that are mostly bound to dietary fiber or protein that remains insoluble in the usual solvent and requires an extra step of hydrolysis during extraction to make them soluble and bioavailable.

Phenolic compounds can have varying degrees of bioavailability based on their structure, food processing and matrix characteristics, and the host, among others. For example, bioavailability of phenols varies over a wide range from 0.3% estimated for anthocyanins to 43% in the case of isoflavones.

Hydrolysable tannins and proanthocyanidins are polyphenols that have a high degree of extraction from the food and thus bioavailability to the host. The bioactivity of tannins is thought to depend on the degree of polymerization and their solubility in the gut, for example, highly polymerized tannins have low bioaccessibility in the small intestine and are not easily fermented by colonic microflora. Low rates of fermentation reduce the bioavailability of downstream metabolites, for example urolithins. In some embodiments, the present disclosure describes a composition administered to modify or increase the bioavailability of urolithins in the gut.

In some embodiments, a method is a method of increasing the bioavailability of an ellagitannin composition for a subject. In some embodiments, a method comprises determining a bioavailability level of an ellagitannin of the ellagitannin composition in the gut of a subject. In some embodiments, a method comprises comparing the bioavailability level of the ellagitannin of the ellagitannin composition in the gut of the subject to a reference level. In some embodiments, a reference level is a historical bioavailability reference level for an ellagitannin, a bioavailability level of an ellagitannin in the gut of the subject prior to receiving a combination; or bioavailability level of an ellagitannin in the gut of a comparable subject who has not received the combination.

In some embodiments, a method comprises determining a level of the urolithin produced in plasma of a subject. In some embodiments, a method comprises comparing the level of the urolithin in plasma of a subject to a reference level. In some embodiments, a reference level is a concentration of urolithin in plasma, e.g., 0.2-20 µM (Espin J C, Larrosa M, Garcia-Conesa M T, Tomás-Barberán F. Biological significance of urolithins, the gut microbial ellagic Acid-derived metabolites: the evidence so far. Evid Based Complement Alternat Med. 2013; 2013:270418. doi: 10.1155/2013/270418, which is incorporated herein by reference). In some embodiments, a reference level is a concentration of urolithin in plasma of at least 0.1 µM, at least 0.2 µM, at least 0.5 µM, at least 1 µM, at least 5 µM, at least 10 µM, or at least 15 µM. In some embodiments, a reference level is a concentration of urolithin in plasma of at least 0.5 µM, at most 1 µM, at most 5 µM, at most 10 µM, at most 15 µM, at most 20 µM, or at most 25 µM.

In some embodiments, a reference level, whether in gut or plasma, is a historical reference level of a urolithin, a urolithin level of in the gut of the subject prior to receiving a combination, or a urolithin level of in the gut of a comparable subject who has not received a combination.

The concentration of urolithin A can reach up to micromolar (µM) levels in plasma without any apparent toxic effects in vivo. For example, upon consumption of pomegranate juice by humans, peak plasma levels of UA can reach 14 to 40 µM, but there may be wide variations among individuals (see, e.g., Cerda et al., Eur. J. Nut. 43: 205-220, which is incorporated herein by reference). Wide interindividual variation is likely due to differences in microbiota. Selma et al. identified mono-cultured bacteria (*Gordonibacter* lurolithinfaciens and *Gordonibacter pamelaeae* DSM 19378T) that can metabolize ellagic acid to produce luteic acid, urolithin M-5, urolithin M-6 and urolithin C. However, these cultured bacteria were incapable of producing downstream products, urolithin A and urolithin B; see Selma et al., Food & Nut. 5: 1779-1784 (2014), which is incorporated herein by reference.

Methods of Treatment

The present disclosure recognizes that compositions described herein can be useful in the treatment of subjects. Methods provided by the present disclosure include methods for the treatment of certain diseases, disorders and conditions. In some embodiments, relevant diseases, disorders and conditions may be or include liver diseases and conditions or disorders associated with mitochondrial dysfunction.

Generally, methods of treatment provided by the present disclosure involve administering a therapeutically effective amount of a probiotic alone or in combination with a ellagitannin composition as described herein to a subject who is in need of, or who has been determined to be in need of, such treatment.

In some embodiments, methods of treatment provided herein are therapeutic, e.g., may be administered to subjects after development of significant symptoms of diseases or disorders associated with mitochondrial dysfunction.

In some embodiments, provided methods of treatment are administered to a subject that is a mammal, e.g., a mammal that experiences a disease, disorder, or condition as described herein; in some embodiments, a subject is a human or non-human veterinary subject, e.g., an ape, cat, dog, monkey, or pig.

In many embodiments, "treatment" involves ameliorating at least one symptom of a disease, disorder, or condition associated with diseases or disorders associated with mitochondrial dysfunction. In some embodiments, a method of treatment can be prophylactic.

In some embodiments, the methods can include administration of a therapeutically effective amount of a probiotic and/or ellagitannin composition before, during (e.g., concurrently with), or after administration of a treatment that is expected to be associated with liver disease or disorders associated with mitochondrial dysfunction.

In some embodiments, the compositions described herein can be administered in a form containing one or more pharmaceutically acceptable carriers. Suitable carriers have been described previously and vary with the desired form and mode of administration of a composition. For example, pharmaceutically acceptable carriers can include diluents or excipients such as fillers, binders, wetting agents, disintegrators, surface-active agents, glidants, and lubricants. Typically, a carrier may be a solid (including powder), liquid, or any combination thereof. Each carrier is preferably "acceptable" in the sense of being compatible with other ingredients in the composition and not injurious to a subject. A carrier can be biologically acceptable and inert (e.g., it permits the composition to maintain viability of the biological material until delivered to the appropriate site).

Oral compositions can include an inert diluent or an edible carrier. For purposes of oral therapeutic administration, an active compound can be incorporated with excipients and used in the form of tablets, lozenges, pastilles, troches, or capsules, e.g., gelatin capsules. Oral compositions can also be prepared by combining a composition of the present disclosure with a food. In some embodiments, microbes can be formulated in a food item. Some non-limiting examples of food items to be used with the methods and compositions described herein include: popsicles, cheeses, creams, chocolates, milk, meat, drinks, pickled vegetables, kefir, miso, sauerkraut, etc. In other embodiments, food items can be juices, refreshing beverages, tea beverages, drink preparations, jelly beverages, and functional beverages; alcoholic beverages such as beers; carbohydrate-containing foods such as rice food products, noodles, breads, and pastas; paste products such as fish, hams, sausages, paste products of seafood; retort pouch products such as curries, food dressed with a thick starchy sauce, and Chinese soups; soups; dairy products such as milk, dairy beverages, ice creams, and yogurts; fermented products such as fermented soybean pastes, fermented beverages, and pickles; bean products; various confectionery products including biscuits, cookies, and the like, candies, chewing gums, gummies, cold desserts including jellies, cream caramels, and frozen desserts; instant foods such as instant soups and instant soy-bean soups; and the like. It is preferred that food preparations not require cooking after admixture with microbial strain(s) to avoid killing any microbes.

In one embodiment a food used for administration is chilled, for example, iced flavored water. In certain embodiments, the food item is not a potentially allergenic food item (e.g., not soy, wheat, peanut, tree nuts, dairy, eggs, shellfish or fish). Pharmaceutically compatible binding agents, and/or adjuvant materials can be included as part of the composition. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, orange flavoring, or other suitable flavorings. These are for purposes of example only and are not intended to be limiting.

In a related embodiment, the compositions described herein are contemplated to comprise one or more microbes as described herein in combination with a viable lactic acid bacteria in combination with any material to be absorbed, including but not limited to nutrient supplements, foodstuffs, vitamins, minerals, medicines, therapeutic compositions, antibiotics, hormones, steroids, and the like compounds where it is desirable to insure efficient and healthy absorption of materials from the gastrointestinal tract into the blood. The amount of material included in the composition can vary widely depending upon the material and the intended purpose for its absorption, such that the composition is not to be considered as limiting.

Pharmaceutical Compositions

Provided herein are compositions comprising probiotic microbes or combinations of probiotic microbes and ellagitannin compositions. In some embodiments, such compositions are used to treat liver diseases or disorders associated with mitochondrial dysfunction in a subject. In some embodiments, compositions for use in accordance with the present disclosure are pharmaceutical compositions, e.g., for administration (e.g., oral administration) to a mammal (e.g., a human). Pharmaceutical compositions typically include an active agent (e.g., individual microbial strains or combinations of microbial strains with ellagitannin compositions), and a pharmaceutically acceptable carrier. Certain exemplary pharmaceutically acceptable carriers include, for instance saline, solvents, dispersion media, coatings, antibacterial and antifungal agents, isotonic and absorption delaying agents, and the like, compatible with pharmaceutical administration.

In some embodiments, a pharmaceutical composition for use in accordance with the present disclosure may include and/or may be administered in conjunction with, one or more supplementary active compounds; in certain embodiments, such supplementary active agents can include ginger, curcumin, probiotics (e.g., probiotic strains of one or more of the following genera: *Lactobacillus, Bifidobacterium, Saccharomyces, Enterococcus, Streptococcus, Pediococcus, Leuconostoc, Bacillus,* and/or *Escherichia coli* (see Fij an, Int J Environ Res Public Health. 2014 May; 11(5): 4745-4767, which is incorporated herein by reference); prebiotics (nondigestible food ingredients that help support growth of probiotic microbes, e.g., fructans such as fructooligosaccharides (FOS) and inulins, galactans such as galactooligosaccharides (GOS), dietary fibers such as resistant starch, pectin, beta-glucans, and xylooligosaccharides (Hutkins et al., Curr Opin Biotechnol. 2016 February; 37: 1-7, which is incorporated herein by reference) and combinations thereof.

Pharmaceutical compositions are typically formulated to be compatible with their intended route of administration. Examples of routes of administration include oral administration. Methods of formulating suitable pharmaceutical compositions have been reported, see, e.g., *Remington: The Science and Practice of Pharmacy,* 21st ed., 2005; and the books in the series *Drugs and the Pharmaceutical Sciences: a Series of Textbooks and Monographs* (Dekker, NY). Oral compositions generally include an inert diluent or an edible carrier. To give but a few examples, in some embodiments, an oral formulation may be or comprise a syrup, a liquid, a tablet, a troche, a gummy, a capsule, e.g., gelatin capsules, a powder, a gel, a film, etc.

In some embodiments, pharmaceutically compatible binding agents, and/or adjuvant materials can be included as part of a pharmaceutical composition. In some particular embodiments, a pharmaceutical composition can contain, e.g., any one or more of the following inactive ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. In some embodiments, the compositions can be taken as-is or sprinkled onto or mixed into a food or liquid (such as water). In some embodiments, a composition that may be administered to mammals as described herein may be or comprise an ingestible item (e.g., a food or drink) that comprises (e.g., is supplemented) with an individual microbial strain or combinations of microbial strains from a mammalian microbiome, extracts thereof, and/or components thereof.

In some embodiments, a food can be or comprise one or more of bars, candies, baked goods, cereals, salty snacks, pastas, chocolates, and other solid foods, as well as liquid or semi-solid foods including yogurt, soups and stews, and beverages such as smoothies, shakes, juices, and other carbonated or non-carbonated beverages. In some embodiments, foods are prepared by a subject by mixing in individual microbial strains or combinations of microbial strains from a mammalian microbiome, extracts thereof, and/or components thereof.

Compositions can be included in a kit, container, pack, or dispenser, together with instructions for administration or for use in a method described herein.

Those skilled in the art, reading the present disclosure, will appreciate that, in some embodiments, a composition (e.g., a pharmaceutical composition) as described herein may be or comprise one or more cells, tissues, or organisms (e.g., plant or microbe cells, tissues, or organisms) that produce (e.g., have produced, and/or are producing) a relevant compound.

In some embodiments, an individual microbial strain or combinations of microbial strains from a mammalian microbiome that have been killed (e.g., heat killed). Alternatively, in some embodiments, an individual microbial strain or combinations of microbial strains from a mammalian microbiome may include cells that are viable or alive.

In some embodiments, methods of treatment as described herein involve administering a viable or living individual microbial strain or combinations of microbial strains from a mammalian microbiome. In some such embodiments, a viable or living individual microbial strain or combinations of microbial strains from a mammalian microbiome is administered according to a regimen that achieves population of the subject's microbiome with administered cells.

In some embodiments, a viable or living individual microbial strain or combinations of microbial strains from a mammalian microbiome as described herein comprises and/or is formulated through use of one or more cell cultures and/or supernatants or pellets thereof, and/or a powder formed therefrom.

In some embodiments, a pharmaceutical composition provided herein can promote the colonization of an individual microbial strain or combinations of microbial strains from a mammalian microbiome, particularly microbial strain(s) that have been identified, characterized, or assessed as decreasing the severity or incidence of a mammalian disease or condition, in a mammal suffering from or at risk of the mammalian disease or condition. In some embodiments, a pharmaceutical composition provided herein can attenuate the colonization of an individual microbial strain or combinations of microbial strains from a mammalian microbiome, particularly microbial strain(s) that have been identified, characterized, or assessed as increasing the severity or incidence of a mammalian disease or condition, in a mammal suffering from or at risk of the mammalian disease or condition. In some embodiments, a pharmaceutical composition provided herein can promote the colonization of an individual microbial strain or combinations of microbial strains from a mammalian microbiome, particularly microbial strain(s) that have been identified, characterized, or assessed as not affecting the severity or incidence of the mammalian disease or condition but have been identified, characterized, or assessed as being capable of outcompeting one or more microbial strains that have been identified, characterized, or assessed as increasing the severity or incidence of a mammalian disease or condition, in a mammal suffering from or at risk of the mammalian disease or condition.

In some embodiments, a pharmaceutical composition is tailored to a specific mammal (e.g., a specific human subject) based on that mammal's (e.g., human's) microbiome. In some embodiments, a pharmaceutical composition is specific for a microbiome of a mammalian subject (e.g., human). In some embodiments, a pharmaceutical composition is specific for microbiomes of a population of mammals (e.g., humans). Populations of mammals can include, but are not limited to: families, mammals in the same regional location (e.g., neighborhood, city, state, or country), mammals with the same disease or condition, mammals of a particular age or age range, mammals that consume a particular diet (e.g., food, food source, or caloric intake).

Treatment of Disorders Associated with Mitochondrial Dysfunction

Mitochondrial dysfunction is an inability of mitochondria to undergo the processes associated with normal function, and can arise as a result of, e.g., issues with electron transport and ATP synthesis, lack of essential substrates, or low number of mitochondria in the cell. A number of mitochondrial disorders are associated with mitochondrial dysfunction, including, for example, mitochondrial myopathy, diabetes mellitus and deafness (DAD), Leber's hereditary optic neuropathy, Leigh syndrome, myoneurogenic gastrointestinal encephalopathy, myoclonic epilepsy with Ragged Red Fibers, mitochondrial DNA depletion syndrome, Alzheimer's Dementia, Parkinson's disease, Huntington Disease, Amyotrophic Lateral Sclerosis (ALS), mental retardation, deafness and blindness, diabetes, obesity, cardiovascular disease, stroke and autoimmune diseases such as multiple sclerosis, Sjogrens syndrome, lupus and rheumatoid arthritis.

Mitophagy is an autophagy process that specifically targets non- or dysfunctional mitochondria and is crucial for maintaining mitochondrial homeostasis. Nutrient levels and nutritional stressors can lead to changes in mitophagy-related mitochondrial turnover and impact overall mitochondrial function. Urolithin A can induce mitophagy in muscular and intestinal tissue while also boosting mitochondrial biogenesis, leading to improved mitochondrial function. In some embodiments, the present disclosure describes methods of treatment of mitochondrial disorders and compositions designed for said treatment.

Many human diseases are known to be associated with dysfunctional mitochondria, including, but not limited to, various cancers, neurodegenerative diseases, and metabolic disorders. In some embodiments, the present disclosure can lead to changes in mitochondrial function to improve overall health. For example, in certain embodiments, the present disclosure describes improving mitochondrial function through increasing the bioavailability of various nutrients, including, but not limited to, ellagitannins and their associated metabolites.

Treatment Polyglutamine (polyQ) Diseases

Expanded polyglutamine (polyQ) proteins can aggregate intracellularly, e.g., in age-related neurodegenerative disorders including (among others) Huntington's disease. Generally, polyQ diseases are characterized by a genetic mutation in cytosine-adenine-guanine triplet repeat expansion. The mutation leads to extended repeat elements of protein causing polyQ extension. These diseases are characterized by cognitive impairment, resulting from progressive loss of neuronal function. The exact mechanistic details on the cause of expanded polyQ toxicity are not fully understood. The striking phenotype is an aggregation of expanded polyQ proteins. Different cellular pathways including lysosomal degradation pathway, autophagy and proteasome degradation are known to promote clearance of polyQ protein. In some embodiments, disclosure describes the discovery our product formulation (pome extract and *L. plantarum* MBT501) mitigating the polyQ aggregates in transgenic worms expressing polyQ repeats.

Methods provided herein can comprise administering to a subject an ellagitannin composition, an enzymatic composition comprising one or more ellagitannin enzymes, or a combination as disclosed herein so that the subject is receiving a combination disclosed herein. In some embodiments, a method is a method of decreasing the formation of polypeptide aggregates in a cell or tissue. In some embodiments, a method is a method of decreasing an amount of polypeptide aggregates in a cell or tissue. In some embodiments, polypeptide aggregates are aggregates of polypeptide comprising a polyQ region (i.e., polyQ aggregates). In some embodiments, a polyQ region comprises at least 10, at least 20, at least 30, at least 40, or at least 50 glutamines. In some embodiments, a cell is or comprises neurons. In some embodiments, a cell is or comprises central nervous system tissue.

In some embodiments, a method comprises determining a level of polypeptide aggregate formation in a cell or tissue. In some embodiments, a method comprises determining a level of polypeptide aggregate formation in a cell or tissue. In some embodiments, a method comprises comparing a level of polypeptide aggregate formation in a cell or tissue to a reference level of polypeptide aggregate formation in a cell or tissue. In some embodiments, a reference level is determined in a cell or tissue of a subject that has not been administered an ellagitannin composition, an enzymatic composition comprising one or more ellagitannin enzymes, or a combination as disclosed herein. In some embodiments, a method comprises, prior to administration, determining a level of polypeptide aggregate formation in a cell or tissue. In some embodiments, a method comprises, following administration, determining a level of polypeptide aggregate formation in a cell or tissue. In some embodiments, a method comprises comparing a level of polypeptide aggregate formation in a cell or tissue determined prior to administration with a level of polypeptide aggregate formation in a cell or tissue determined following administration.

In some embodiments, a method comprises determining a level of polypeptide aggregates in a cell or tissue. In some embodiments, a method comprises determining a level of polypeptide aggregates in a cell or tissue. In some embodiments, a method comprises comparing a level of polypeptide aggregates in a cell or tissue to a reference level of polypeptide aggregates in a cell or tissue. In some embodiments, a reference level is determined in a cell or tissue of a subject that has not been administered an ellagitannin composition, an enzymatic composition comprising one or more ellagitannin enzymes, or a combination as disclosed herein. In some embodiments, a method comprises, prior to administration, determining a level of polypeptide aggregates in a cell or tissue. In some embodiments, a method comprises, following administration, determining a level of polypeptide aggregates in a cell or tissue. In some embodiments, a method comprises comparing a level of polypeptide aggregates in a cell or tissue determined prior to administration with a level of polypeptide aggregates in a cell or tissue determined following administration.

Treatment of Liver Diseases

Antioxidant therapy has been considered to be beneficial for use in treating various diseases, including those of the liver. Levels of antioxidant compounds in the body can be influenced by the Nrf2 protein, which has been shown to have a role in liver diseases such as non-alcoholic steatohepatitis, acute hepatoxicity, non-alcoholic fatty liver disease, alcoholic liver disease, viral hepatitis, liver fibrosis, hepatic IRI, and some liver cancers. Low levels of Nrf2 expression has been reported to be associated with decreased anti-oxidant activity in the cell. Administration of ellagitannins can have positive effects on liver health and reduce oxidative damage, for example by protecting liver cells from ethanol-induced cellular damage through increased Nrf2 expression to reduce oxidative stress. In some embodiments, the present disclosure describes methods of treatment of various liver diseases through administration of ellagitannins and/or probiotic compositions either alone or combination. In some embodiments, said treatment increases expression of Nrf2 in a liver cell, promoting antioxidant activity in the cell and thereby promoting liver health or function.

Nuclear factor (erythroid-derived 2)-like 2 (NRF2) is a transcription factor that regulates the expression of antioxidant proteins that protect against oxidative damage triggered by injury or inflammation. When a cell is not in a state of stress, NRF2 is retained in the cytoplasm by the cytoplasmic inhibitor KEAP (Kelch-like ECH associated protein 1) and degraded quickly. However, when a cell is under oxidative stress, NRF2 is not degraded and localizes to the nucleus to induce expression of antioxidative gene products. Nuclear localization of NRF2 can be used as an indirect measure of NRF2 activity. However, as has been reported, an easier method for determining NRF2 activity is by assessing expression levels of genes that are positively regulated by NRF2. Such genes include but are not limited to, NAD(P)H quinone oxidoreductase 1 (Nqo1), glutamate-cysteine ligase, sulfiredoxin 1 (SRXN1), thioredoxin reductase 1 (TXNRD1), heme oxygenase-1 (HMOX1, H001), glutathione S-transferase (GST), UDP-glucuronosyltransferase (UGT), and multidrug resistance-associated proteins (Mrps).

The present disclosure provides methods comprising administering to a subject an ellagitannin composition, an enzymatic composition comprising one or more ellagitannin enzymes, or a combination as disclosed herein so that the subject is receiving a combination disclosed herein. In some embodiments, a method is a method of modifying an expression level or an activity level of Nrf2 in a cell or tissue of a subject. In some embodiments, a method is a method of increasing the expression level or the activity level of Nrf2 in the cell or tissue of the subject.

In some embodiments, a method comprises determining the expression level or the activity level of nuclear respiratory factor-2 (Nrf2) in the cell or tissue of the subject. In some embodiments, a method comprises comparing the expression level or the activity level of Nrf2 in the cell or tissue to a reference level. In some embodiments, a reference level is a historical expression or activity level of Nrf2, an expression level or an activity level of nuclear respiratory factor-2 (Nrf2) in a comparable cell or tissue of the subject prior to receiving the combination, or an expression level or an activity level of nuclear respiratory factor-2 (Nrf2) in a comparable cell or tissue of a comparable subject who has not received the combination. In some embodiments, a method comprises determining an expression level or an activity level of a gene regulated by Nrf2 expression in a cell or tissue of the subject.

Antioxidant compounds within the body are capable of protecting organisms from reactive processes that involve reactive oxygen and nitrogen species (ROS, RNS). These compounds can protect the human body from oxidative stress, which is associated with human diseases including, but not limited to, atherosclerosis, diabetes mellitus, chronic inflammation, neurodegenerative disorders, and certain cancers. In some embodiments, the present disclosure describes a composition and method of administration to modify antioxidant levels in the body. In some embodiments, a method comprises determining a level of one or more antioxidants in a cell or tissue of the subject. In some embodiments, a cell or tissue of a subject comprises a liver cell or liver tissue. In some embodiments, a method comprises measuring an indicator of liver health or function in a subject.

Methods of Increasing Shelf-Life

Storage methods for improved shelf-life of prebiotics and/or probiotics can vary depending on the organism involved. Often, probiotic formulations with dairy can be challenging to store while remaining stable and palatable. In some embodiments, the present disclosure describes a method for increasing the shelf-life of a probiotic composition through the use of one or more fruit extracts. In some embodiments, a method of increasing the viable shelf-life of a probiotic product comprising an EES microbe as described herein includes adding an ellagitannin composition as described herein to the probiotic product, where the EES microbe expresses one or more ellagitannin enzymes described herein.

EXAMPLES

The following examples are provided so as to describe to the skilled artisan how to make and use methods and compositions described herein, and are not intended to limit the scope of the present disclosure.

Example 1

This example demonstrates the identification of a bacterium, *Lactobacillus plantarum*, that induces the gst-4 expression in *C. elegans* transcriptional fusion reporter CL2166 dvIs19 [pAF15 (gst-4::gfp-nls)] III[1,2] using a qualitative visual screen. gst-4 encodes glutathione-S-transferases (GSTs), an antioxidant gene which is regulated by skn-1, a homologue of Nrf2, a transcription factor plays a vital role in anti-oxidant pathway in human. The transcription factor skn-1, has been reported in regulating a variety of anti-oxidant genes including the anti-oxidant gene gst-4[3].

A transgenic strain CL2166 was used that expresses GFP only in hypodermal cells when fed on *E. coli* OP50 and pome extract only. *E. coli* OP50 was used as a control, as it is a standard microbial strain on which *Caenorhabditis elegans* are typically grown in the laboratory. The bacterium *L. plantarum* alone induced some expression in the intestine of worms. The treatment of *L. plantarum* and Pome extract in a transgenic strain CL2166 that expresses GFP induced the GFP expression in throughout intestines and body of the worm (FIG. 1).

Example 2

Figure 2:
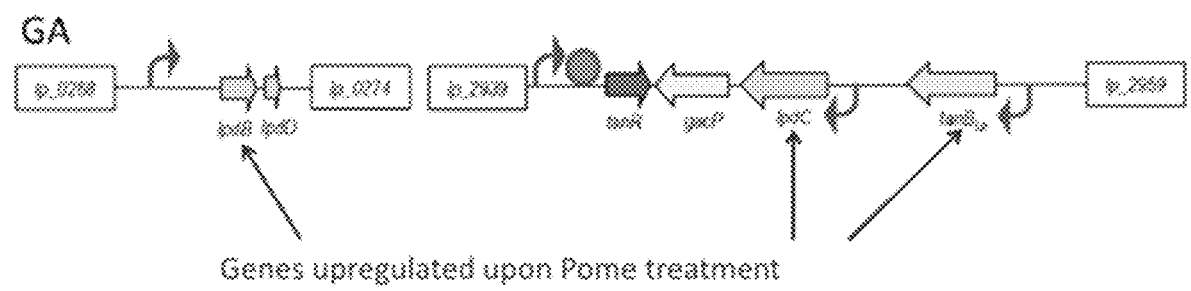
FIG. 2, panel (A) includes a schematic of a cluster of genes involved in ellagitannin metabolism.
Figure 2:
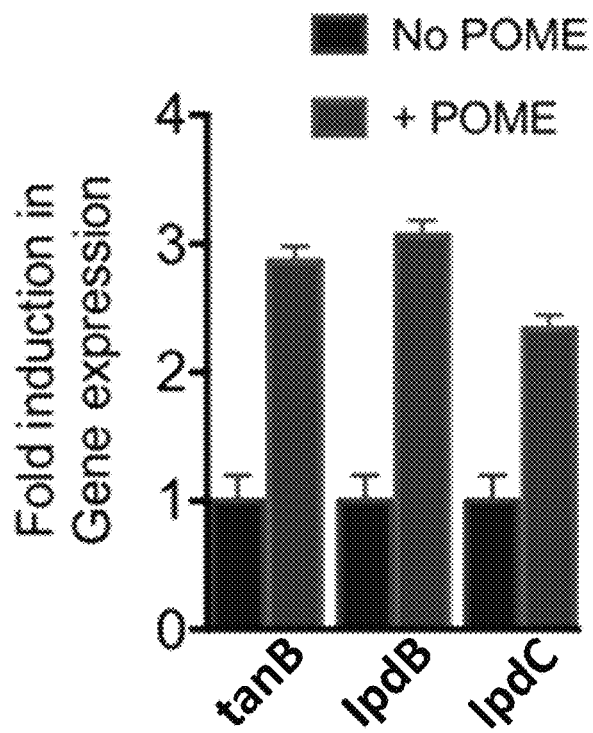

Genes encoding enzymes of tannase (tan B), gallate decarboxylase (lpdB) and gallate decarboxylase (lpdC) were tested to determine whether the enzymes are involved in ellagitanin metabolism[4,5]. *L. plantarum* possesses the decarboxylase enzyme, which is involved in the degradation polyphenolic compounds including pome extracts, berry extracts and walnut extracts[6,7] (FIG. 2a). The effect of pome extract or polyphenolic compounds on the expression of genes encoding enzymes of tannase (tan B), gallate decarboxylase (lpdB) and gallate decarboxylase (lpdC) was observed by qPCR. The prebiotic pome extract treatment greatly induced (>3-fold) the expression of the tannase (tan B), gallate decarboxylase (lpdB) and gallate decarboxylase (lpdC) (FIG. 2b).

Example 3

Figure 3:
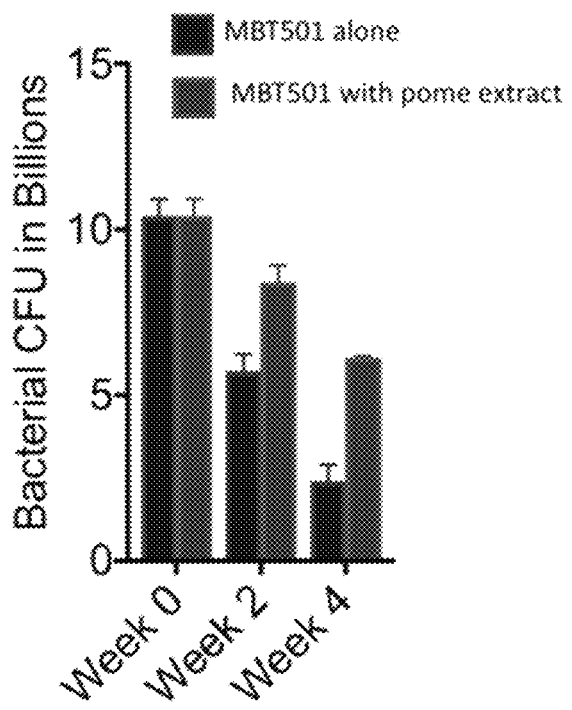
FIG. 3, panel (A) includes a bar graph showing colony forming units of *L. plantarum* (MBT501) at 0, 2, and 4 weeks alone (black bars) or with pome extract (gray bars).
Figure 3:
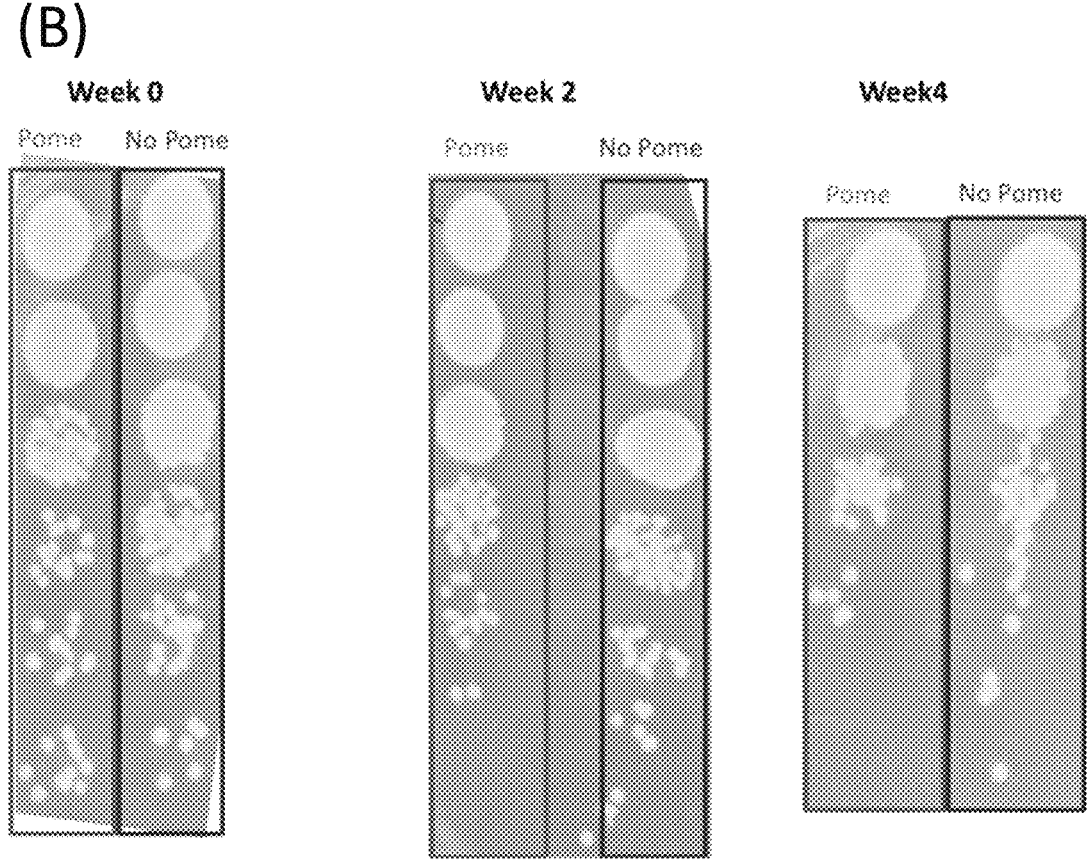

In this method, the prebiotic pome extract was tested to determine if it can aid in the maintenance of *L. plantarum*, e.g., enhance the shelf life of the bacterium. The pome extract was found to increase the shelf life of *L. plantarum*. so as to maintain the bacterium *L. plantarum* count in a beneficial manner. The pome extract treated *L. plantarum* showed the same count (10 billion CFU) for 4 weeks. In contrast, bacteria alone showed little greater than half of the initial count (FIGS. 3a and b).

Example 4

Figure 4:
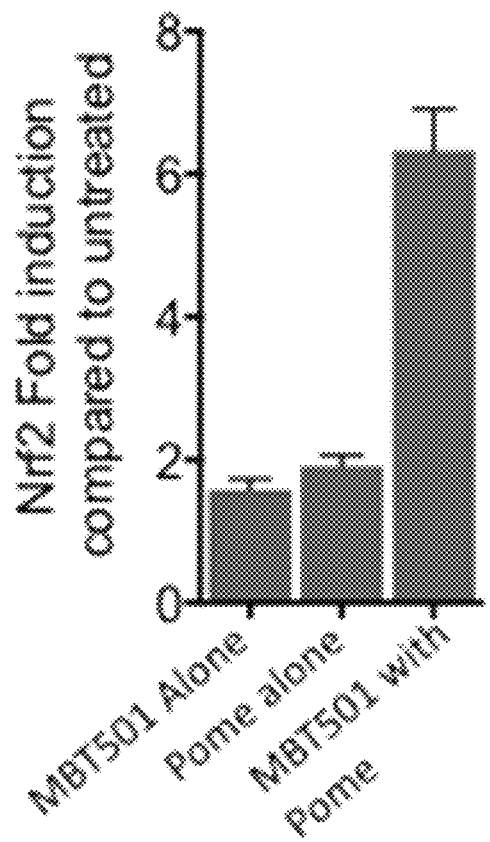
FIG. 4, panel (A) includes a bar graph showing induction levels of Nrf2 expression using reporter Nrf2:Luciferase in a human liver cell line (HepG) treated with *L. plantarum* (MBT501) alone, pome extract alone, or *L. plantarum* (MBT501) and pome extract.
Figure 4:
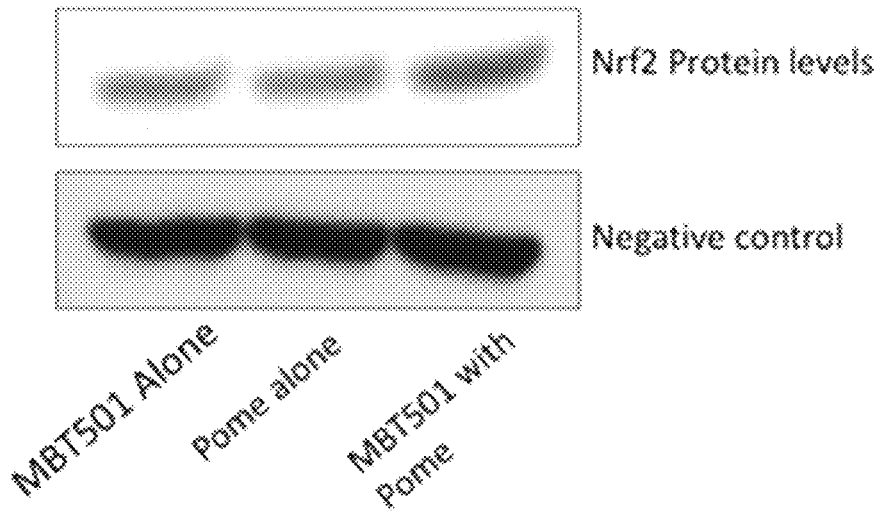

The human liver cell line (HepG) was used with stable expression of a Nrf2-luciferase reporter gene to observe Nrf2 induction. This cell line exhibited an increase in luciferase activity in response to the treatment of pome extract with *L. plantarum*. The luciferase activity was increased to 3-fold within 24 hours of treatment, compared to bacteria and pome extract alone (FIG. 4a).

Also, the Nrf2 induction was confirmed by western blot analysis of cellular lysates. In a whole cell extract, an increase in Nrf2 protein expression by the treatment of *L. plantarum* with pome was demonstrated. This increase was specific for Nrf2 because there was no change in actin expression. In contrast, there was no change in Nrf2 expression of cell lysate prepared that was treated with *L. plantarum* and pome extract alone (FIG. 4b).

Example 5

This example demonstrates the combination of bacterium, *L. plantarum* MBT501 and pome extract, mitigated polyQ aggregates of rmls133 (unc_54p::Q40::YFP) in *C. elegans* using a qualitative visual screen. Young adult worms showed that the formation of up to 140 aggregates PolyQ40 repeats directly correlates with the observation of human disease. Such aggregates can contribute to cytoplasmic toxicity and neurodegenerative diseases (Morley J F, Brignull H R, Weyers J J, Morimoto R I. The threshold for polyglutamine-expansion protein aggregation and cellular toxicity is dynamic and influenced by aging in *Caenorhabditis elegans*. *Proc Natl Acad Sci USA*. 2002 Aug. 6; 99(16):10417-22. doi: 10.1073/pnas.152161099. Epub 2002 Jul. 16. PMID: 12122205, PMCID: PMC124929; Kailiang Jia, Anne C. Hart & Beth Levine (2007) Autophagy Genes Protect Against Disease Caused by Polyglutamine Expansion Proteins in *Caenorhabditis elegans*, Autophagy, 3:1, 21-25, DOI: 10.4161/auto.3528; Kokona B, May C A, Cunningham N R, et al. Studying polyglutamine aggregation in *Caenorhabditis elegans* using an analytical ultracentrifuge equipped with fluorescence detection. *Protein Sci*. 2016; 25(3):605-617, doi:10.1002/pro.2854, each of which is incorporated herein by reference.

Figure 5:
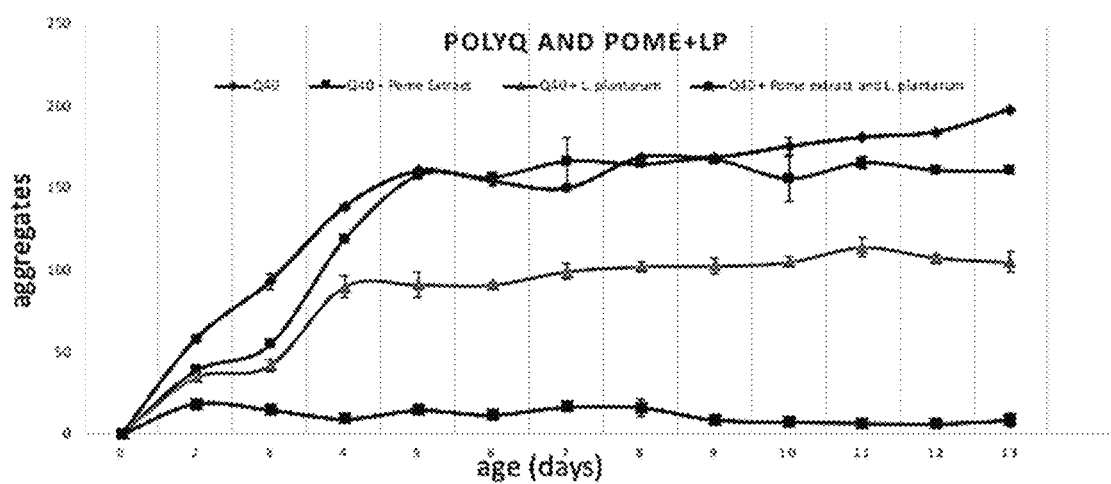
FIG. 5 includes a line graph showing the number of polyQ aggregates formed when using reporter rmIs133 (unc_54p::Q40::YFP) in *C. elegans* fed negative control bacteria, pome extract, fed on *L. plantarum* (MBT501), and fed on *L. plantarum* (MBT501) and pome extract. The aggregates were determined using a qualitative visual screen.

PolyQ40 repeats fused with YFP were expressed in the cytoplasm of body wall muscles in the worms (transgenic strain unc_54p::Q40::YFP). The worms were fed: (1)*E. coli* OP50, pome extract, (2) *L. plantarum* (MBT501), or (3) *L. plantarum* (MBT501) and pome extract. *E. coli* OP50 was used as a control, as it is a standard microbial strain on which *C. elegans* are typically grown in the laboratory. As shown, the bacterium *L. plantarum* alone mitigated the formation of PolyQ40 aggregates to some level. Treatment of *L. plantarum* and Pome extract was shown to mitigate expression of the PolyQ40 aggregates (FIG. 5).

OTHER EMBODIMENTS

It is to be appreciated by those skilled in the art that various alterations, modifications, and improvements to the present disclosure will readily occur to those skilled in the art. Such alterations, modifications, and improvements are intended to be part of the present disclosure, and are intended to be within the spirit and scope of the invention. Accordingly, the foregoing description and drawing are by way of example only and any invention described in the present disclosure if further described in detail by the claims that follow.

Those skilled in the art will appreciate typical standards of deviation or error attributable to values obtained in assays or other processes as described herein. The publications, websites and other reference materials referenced herein to describe the background of the invention and to provide additional detail regarding its practice are hereby incorporated by reference in their entireties.

It is to be understood that while embodiments of the invention have been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A combination comprising:
    (a) an ellagitannin composition; and
    (b) an enzymatic composition comprising an ellagitannin-enzyme-synthesizing (EES) microbe or an extract thereof and one or more ellagitannin enzymes,
    wherein the EES microbe is *Lactobacillus plantarum* MBT501;
    wherein the one or more ellagitannin enzymes are selected from the group consisting of a tannin acyl hydrolase enzyme, a gallate decarboxylase enzyme, and a combination thereof; and
    wherein the shelf-life of the combination is increased to at least 4 weeks relative to a combination without the ellagitannin composition.

2. The combination of claim 1, wherein the one or more ellagitannin enzymes comprises a tannin acyl hydrolase enzyme.

3. The combination of claim 2, wherein the tannin acyl hydrolase enzyme is a tanB tannase enzyme.

4. The combination of claim 1, wherein the one or more ellagitannin enzymes comprises a gallate decarboxylase enzyme.

5. The combination of claim 4, wherein the gallate decarboxylase enzyme is an lpdB gallate decarboxylase enzyme.

6. The combination of claim 4, wherein the gallate decarboxylase enzyme is an lpdC gallate decarboxylase enzyme.

7. The combination of claim 1, wherein the one or more ellagitannin enzymes comprises an lpdB gallate decarboxylase enzyme and an lpdC gallate decarboxylase enzyme.

8. The combination of claim 1, wherein the one or more ellagitannin enzymes comprises a tanB tannase enzyme, an lpdB gallate decarboxylase enzyme, and an lpdC gallate decarboxylase enzyme.

9. The combination of claim 1, wherein the EES microbe is found in nature.

10. The combination of claim 1, wherein the EES microbe is viable or alive.

11. The combination of claim 1, wherein the EES microbe is lyophilized.

12. The combination of claim 1, wherein the ellagitannin composition is selected from the group consisting of a plant extract of pomegranate, strawberry, raspberry, cranberry, blackberry, cloudberry, artic blackberry, muscadine grapes, guava, a Myrtaceae family fruit, walnut, pecan, chestnut, cashew, almond, pistachio, hazelnut, brazil nut, macadamia red wine aging in oak barrels, muscadine grapes juice, pomegranate juice, tea, cognac, Indian gooseberry, beefsteak fungus, and combinations thereof.

13. The combination of claim 1, comprising a prebiotic.

14. The combination of claim 13, further comprising a fructooligosaccharide, an inulin, an isomaltooligosaccharide, a lactilol, a lactosucrose, a lactulose, a soy oligosaccharide, a transgalactooligosaccharide, a xylooligosaccharide, or a combination thereof.

15. The combination of claim 1, wherein the ellagitannin composition, the enzymatic composition, or both is formulated for oral administration.

16. The combination of claim 15, wherein the formulation for oral administration is a diary product.

17. The combination of claim 1, wherein the combination is a food, a beverage, a feed composition, or a nutritional supplement.

18. The combination of claim 1, wherein the combination is a liquid, syrup, tablet, troche, gummy, capsule, powder, gel, or film.

19. The combination of claim 1, further comprising a pharmaceutically acceptable carrier.

20. The combination of claim 19, wherein the combination is an enteric-coated formulation.

21. The combination of claim 1, wherein the combination includes at least $10^5$ CFU of the EES microbe.

22. A method comprising administering the combination of claim 1 to a subject.

\* \* \* \* \*